US009784665B1

(12) United States Patent
Milici et al.

(10) Patent No.: US 9,784,665 B1
(45) Date of Patent: Oct. 10, 2017

(54) METHODS FOR QUANTITATIVE ASSESSMENT OF MUSCLE FIBERS IN MUSCULAR DYSTROPHY

(71) Applicant: Flagship Biosciences, Inc., Westminster, CO (US)

(72) Inventors: Anthony J. Milici, Branford, CT (US); George David Young, Ridgway, CO (US); Holger Lange, Enger (DE); Joseph Krueger, Andover, MA (US); Nathan T. Martin, Boulder, CO (US)

(73) Assignee: Flagship Biosciences, Inc., Westminster, CO (US)

( * ) Notice: Subject to any disclaimer, the term of this patent is extended or adjusted under 35 U.S.C. 154(b) by 97 days.

(21) Appl. No.: 14/983,296

(22) Filed: Dec. 29, 2015

Related U.S. Application Data

(60) Provisional application No. 62/097,543, filed on Dec. 29, 2014.

(51) Int. Cl.
*G06K 9/00* (2006.01)
*G01N 15/14* (2006.01)
*G01N 1/30* (2006.01)
*G01N 33/68* (2006.01)
*G06T 7/00* (2017.01)
*G01N 15/10* (2006.01)
*G01N 15/00* (2006.01)

(52) U.S. Cl.
CPC ........... *G01N 15/1463* (2013.01); *G01N 1/30* (2013.01); *G01N 33/6887* (2013.01);
(Continued)

(58) Field of Classification Search
CPC ........ G01N 1/28; G01N 1/30; G01N 15/1463; G01N 21/64; G01N 21/6428; G01N 21/6456; G01N 21/6458; G01N 21/6486; G01N 21/8851; G01N 33/6887; G01N 23/2076; G01N 2015/0065; G01N 2015/1006; G01N 2015/1465; G01N 2015/1497; G01N 2021/1765; G01N 2021/7786; G01N 2021/8887; *G06K 9/00147* (2013.01); *G06T 7/0012* (2013.01); *G01N 2015/0065* (2013.01); *G01N 2015/1006* (2013.01); *G01N 2015/1465* (2013.01); *G01N 2015/1497* (2013.01); *G01N 2333/4712* (2013.01); *G01N 2800/10* (2013.01); *G06T 2207/10056* (2013.01); *G06T 2207/30004* (2013.01)

(56) References Cited

U.S. PATENT DOCUMENTS 8,957,044 B2 * 2/2015 Childers ................. C12N 9/16
435/320.1
9,314,439 B2 * 4/2016 Iwamoto ............... A61K 31/185
2016/0282338 A1 * 9/2016 Miklas ................... C12M 21/08

* cited by examiner

*Primary Examiner* — Jose Couso
(74) *Attorney, Agent, or Firm* — Coastal Patent Law Group, P.C.

(57) ABSTRACT

The disclosure concerns a method for assessing muscular dystrophy-linked protein expression in muscle fibers using digital image analysis of tissue. The method relates to assessing disease severity in individuals with muscular dystrophy. Muscle tissue samples are obtained from patients submitted for evaluation and processed to produce tissue sections mounted on glass slides which have been stained for a muscular dystrophy-linked protein. Digital images of the stained tissue sections are generated and analyzed by applying an algorithm process implemented by a computer to the images. The algorithm process extracts the morphometric and staining features of the muscular dystrophy-linked protein staining in the tissue, and parameters relating to these features are used to score the disease status for each patient submitted for evaluation. The score of disease status is ultimately used to infer disease severity, monitor the efficacy of a therapeutic approach, or select patients as candidates for a therapeutic approach.

23 Claims, 26 Drawing Sheets

(58) Field of Classification Search
CPC . G01N 2035/00138; G01N 2203/0647; G01N 2203/0652; G01N 2223/076; G01N 2223/0766; G01N 2223/401; G01N 2223/42; G01N 2223/421; G01N 2223/426; G01N 2223/4712; G01N 2800/10; G06K 9/00127; G06K 9/00134; G06K 9/00147; G06K 9/00496; G06K 9/46; G06K 9/4604; G06K 2017/009; G06K 2209/05; G06T 7/0012; G06T 7/0014; G06T 7/0016; G06T 2207/10056; G06T 2207/10064; G06T 2207/10121; G06T 11/60; G06T 2207/30004; G06T 2207/30204; G06T 2210/41; A61B 1/043; A61B 5/0013; A61B 5/0059; A61B 5/0071; A61B 5/14556; A61B 5/4538; A61B 5/48; A61B 6/485; A61B 6/487; A61B 6/5211; A61B 8/5215; A61B 2090/376; A61B 2576/00; G02B 21/34; G02B 21/365
See application file for complete search history.

METHODS FOR QUANTITATIVE ASSESSMENT OF MUSCLE FIBERS IN MUSCULAR DYSTROPHY

CROSS-REFERENCE TO RELATED APPLICATIONS

This application claims benefit of priority with U.S. provisional Ser. No. 62/097,543, filed Dec. 29, 2014; the contents of each of which are hereby incorporated by reference.

BACKGROUND

Field of the Invention

This application relates to methods for assessing immunohistochemistry or immunofluorescence stained muscle tissue with digital image analysis for the purpose of evaluating muscular dystrophy disease status; and more particularly, for digital image analysis-based scoring of protein expression in muscle fibers of tissues obtained from muscular dystrophy patients.

Description of the Related Art

Muscular dystrophy categorizes a group of genetic disorders which result in disorders of the muscles in the human body. Generally speaking, muscular dystrophies are characterized by progressive weakening of skeletal muscles, while additional muscle and organ systems can be impacted during the later courses of the disease. These diseases derive from defective or non-expressed proteins involved in the functional and structural molecular components of muscle fibers. The defects in, or lack of expression of, these proteins are due to mutations in the genes that encode for the respective proteins. Two of the most common forms of muscular dystrophy are Duchenne and Becker muscular dystrophy (DMD and BMD, respectively).

DMD and BMD are rare, recessive disorders deriving from mutation of the DMD gene which encodes the dystrophin protein. The DMD gene is located on the X chromosome and, therefore, DMD and BMD are X-linked disorders that manifest predominately in the male population. In rare cases DMD and BMD are observed in females [Hoffman E P et al. Cell. 1987; 51:919-928. Emery A E, Neuromuscul Disord. 1991; 1:19-29].

DMD results from complete, or near complete, loss of the functional protein product of the DMD gene, while some protein is produced in BMD patients. Dystrophin is a large protein and provides structural stability to muscle cells [Hoffman E P et al. Cell. 1987; 51:919-928.]. The characteristic symptom of DMD and BMD patients is the progressive weakening of muscles. BMD patients, due to the production of some functional protein, generally have milder symptoms than DMD [Bushby K et al. The Lancet Neurology. 2010; 9(1):77-93].

Diagnosis of DMD, BMD and other forms of muscular dystrophy involves genetic testing for mutations in known muscular dystrophy-associated genes and assessment of creatine kinase levels. For example, mutations in the DMD gene indicate DMD and BMD disease. Immunohistochemistry (IHC) assessment of muscle biopsies from suspected patients can also be evaluated [Bushby K et al. The Lancet Neurology. 2010; 9(1):77-93]. In the instances of BMD and DMD, IHC-based evaluation of muscle tissue is performed predominately to understand disease severity, or to distinguish between DMD and BMD, rather than to provide an initial diagnosis of patients.

SUMMARY

Assessment of IHC stained muscle samples is currently performed manually by a pathologist, and is a qualitative or semi-quantitative assessment of the tissue. Initial attempts at using digital image analysis to assess tissue samples from DMD and BMD as model diseases for muscular dystrophy assessment have shown great promise for providing a quantitative assessment of dystrophin levels in patients [Beekman C et al. PLoS ONE, 2014; 9(9):e107494].

Digital image analysis paradigms can enable the generation of quantitative assessments of tissue samples gathered from muscular dystrophy patients. Quantitative assessments of tissue remove the subjective nature of manual scoring paradigms, and may help to better identify distinguishing boundaries of disease severity for muscular dystrophy patients. For example, quantitative assessment of dystrophin protein expression could establish a better understanding of protein expression level differences between DMD and BMD.

More importantly, digital image analysis-based quantitative paradigms can be used to support the development of therapeutic approaches which are designed to modulate muscular dystrophy-linked protein expression by providing a robust and quantitative method for assessing protein levels in patients before, during, and after treatment. Digital image analysis-based quantitative paradigms, especially, hold great promise for evaluating tissue from DMD and BMD patients due to current evaluation of novel therapeutic paradigms for these patients [Fairclough R J et al. Nature Reviews Genetics. 2013; 14:373-378].

Herein, we describe digital image analysis-based methods for quantitatively assessing protein staining in muscle tissue from muscular dystrophy patients; methods that go far beyond the abilities of a manual observer with a microscope and current digital image analysis-based tools. For purposes of example and not limitation, we illustrate the use of the methods described herein for assessing dystrophin expression levels for the purpose of evaluating DMD and BMD disease severity relative to healthy control individuals. It will be apparent to those skilled in the art that these methods can be applied to assess protein expression levels in muscle fibers for additional muscular dystrophy disease types.

In accordance with the embodiments described herein, we describe a method for assessing muscular dystrophy-linked protein expression in muscle fibers using digital image analysis of tissue. The method relates to assessing disease severity in individuals with muscular dystrophy. Muscle tissue samples are obtained from patients submitted for evaluation and processed to produce tissue sections mounted on glass slides which have been stained for a muscular dystrophy-linked protein. Digital images of the stained tissue sections are generated and analyzed by applying an algorithm process implemented by a computer to the images. The algorithm process extracts the morphometric and staining features of the muscular dystrophy-linked protein staining in the tissue, and parameters relating to these features are used to score the disease status for each patient submitted for evaluation. The score of disease status is ultimately used to infer disease severity, monitor the efficacy of a therapeutic approach, or select patients as candidates for a therapeutic approach.

DETAILED DESCRIPTION OF EMBODIMENTS

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention.

Figure 1:
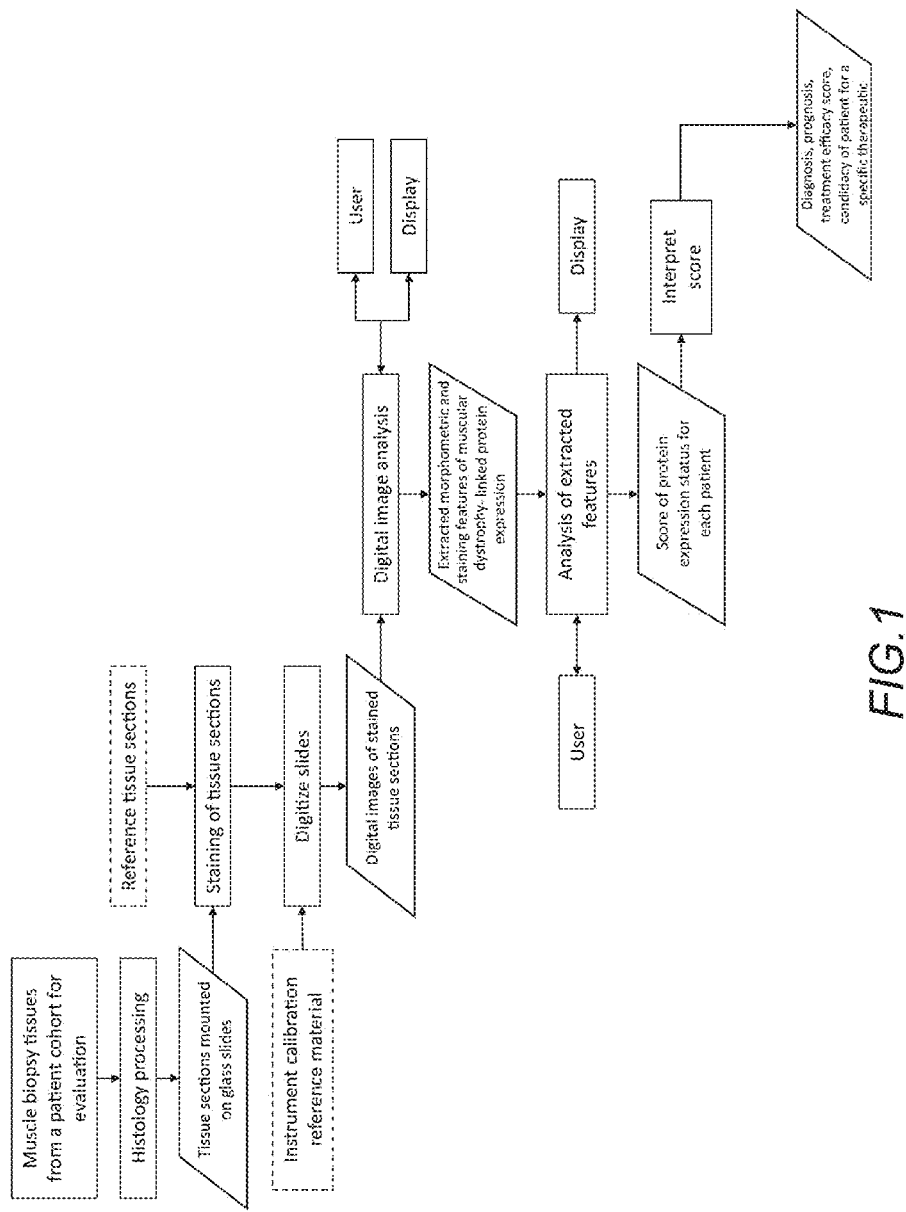
FIG. 1 shows an overview of the method described herein for scoring muscular dystrophy-linked protein expression status in patients submitted for evaluation using a digital image analysis algorithm process implemented by a computer.

In an illustrative embodiment, the method for assessment of muscular dystrophy-linked protein expression in tissue using digital image analysis may generally comprise 8 consecutive steps, including: 1) obtaining muscle tissue embedded in a tissue block from patients submitted for evaluation; 2) processing said tissue block using standard histologic procedures to generate one or more tissue sections attached to a glass histology slide; 3) contacting said tissue sections with one or more antibodies and/or histologic stains to stain said tissue sections; 4) generating digital images of said stained tissue sections; 5) applying an algorithm process implemented by a computer to each digital image; 6) extracting the morphometric and staining features of the tissue section and individual muscle fibers with said algorithm process; 7) assessing one or more of said extracted features to score the disease status for each patient submitted for evaluation; and 8) using said score for the purpose of diagnosis, prognosis, monitoring treatment efficacy, or selecting patients for a specific therapeutic approach. FIG. 1 summarizes the process by which muscular dystrophy-linked protein expression status is evaluated and scored using an algorithm process applied to images of muscle tissue submitted for evaluation.

For purposes of definition, a 'muscular dystrophy-linked protein' is the protein product of a gene known, when mutated or otherwise disrupted, to give rise to one or more form of muscular dystrophy [Kaplan J. C. *Neuromuscular*

*Disorders.* 2011; 21:833-861.]. For purposes of example and not limitation, illustrations of the embodiments of this invention are demonstrated by assessing dystrophin protein expression in muscle tissue obtained from DMD, BMD, or healthy control patients to assess disease status.

Tissue Acquisition and Generating a Tissue Section:

Obtaining tissue for analysis entails collecting a processed biopsy sample from muscle tissue of a patient under evaluation. The tissue obtained from a patient is the 'tissue sample,' and processing of the tissue sample entails fixation of the tissue sample (e.g. using a fixative such as formalin), transporting the sample to a histology laboratory, and generating a tissue block in which the tissue has been embedded in a specified media (e.g. paraffin).

A similar process is followed in the collection and preparation of frozen tissue samples, with the exception that freezing media is utilized instead of fixation media, resulting in a frozen tissue sample which is embedded in a specified media (e.g. OCT) to produce a tissue block.

Once a tissue block is generated which contains the tissue sample, further processing steps are taken to generate a tissue section (e.g. cutting of the tissue block), which is mounted on a glass histology slide using standard and accepted histological procedures.

This tissue preparation process can have a considerable effect on how the tissue features of interest will be expressed in the tissue sections. Careful control needs to be applied to standardizing this process.

Slide Staining:

The slide staining process comprises standard and accepted histological procedures. The staining of the slides (i.e. Hematoxylin and Eosin—H&E, Immunohistochemistry—IHC, immunofluorescence—IF, etc.) highlights the specific cell features of interest in the muscle tissue samples. These features include highlighting muscular dystrophy-linked proteins and additional proteins that identify the structure, or structural components (i.e. muscle fiber membrane), of muscle fibers.

In an illustrative embodiment of this invention, staining (e.g. IF) is performed to highlight dystrophin protein expression in muscle tissue. Dystrophin protein expression is predominately located to the membranes of muscle fibers, and one or more antibodies designed to specifically bind to the dystrophin protein are used to highlight the localization and expression of the protein. The localization and intensity of the one or more antibodies can be visualized using chromogenic (e.g. DAB) stains or immunofluorescence agents (e.g. a secondary antibody labeled with a fluorophore like FITC).

In an embodiment of this invention, staining for a muscular dystrophy-linked protein (e.g. dystrophin) alone is performed. In another preferred embodiment of this invention, staining for a biomarker that highlights the muscle fiber membrane (i.e. merosin, spectrin, etc.) is also performed and visualized using chromogenic (e.g. DAB) or immunofluorescence detection agents (e.g. a secondary antibody labeled with a fluorophore such as FITC) alongside the staining for a muscular dystrophy-linked protein. Additional histologic stains can be optionally utilized to highlight additional cellular compartments (e.g. the nucleus with DAPI or hematoxylin staining).

Once each tissue section is stained, the section is further processed to finalize the preparation of the slide. The histology processing and staining process itself can have a considerable effect on how the cell features of interest are expressed in the tissue sections. Careful control needs to be applied to standardize this process.

Optionally, reference tissue sections can be processed and stained in parallel to the patient samples submitted for evaluation using identical staining conditions. Reference tissue samples can include one or more of: tissue sections that are known positive (i.e. xenograft overexpression model, tissue type known to highly express the protein target, etc.) and negative (i.e. xenograft knockout model, tissue type known to have negative or low expression of the protein target, etc.) controls for staining intensities, tissue sections with a known protein expression level (e.g. human muscle tissue with previously characterized staining levels), and embedded cell pellets with a known level of protein expression (e.g. transfected human cells resulting in a specific level of protein expression).

Figure 2:
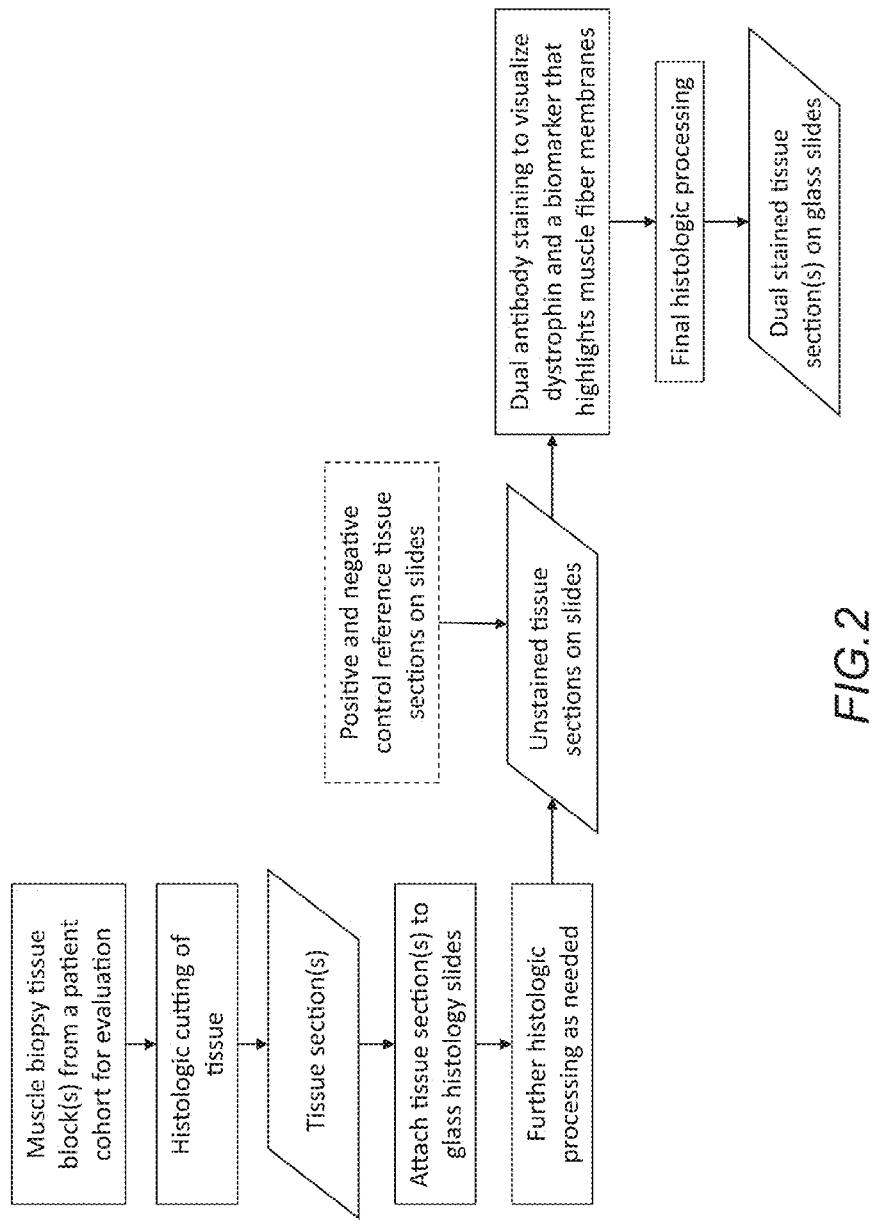
FIG. 2 illustrates the tissue processing and staining steps to generate dual stained tissue sections on glass slides for dystrophin evaluation.

FIG. 2 provides an illustrative example of the preferred embodiment of this invention, whereby muscle biopsy tissue blocks are processed using standard and accepted histology procedures to generate dual biomarker (e.g. dystrophin and a biomarker of the muscle fiber membrane such as merosin) stained tissue sections on glass histology slides. In this preferred embodiment, the staining levels of dystrophin and the biomarker of the muscle fiber membrane are visualized using fluorescently labeled detection probes (i.e. a fluorophore conjugated to the primary antibody). Optionally, reference tissue sections (i.e. positive and negative controls, sections with a known dystrophin expression level, etc.) can be stained in parallel to the patient samples submitted for evaluation as staining controls.

Figure 3:
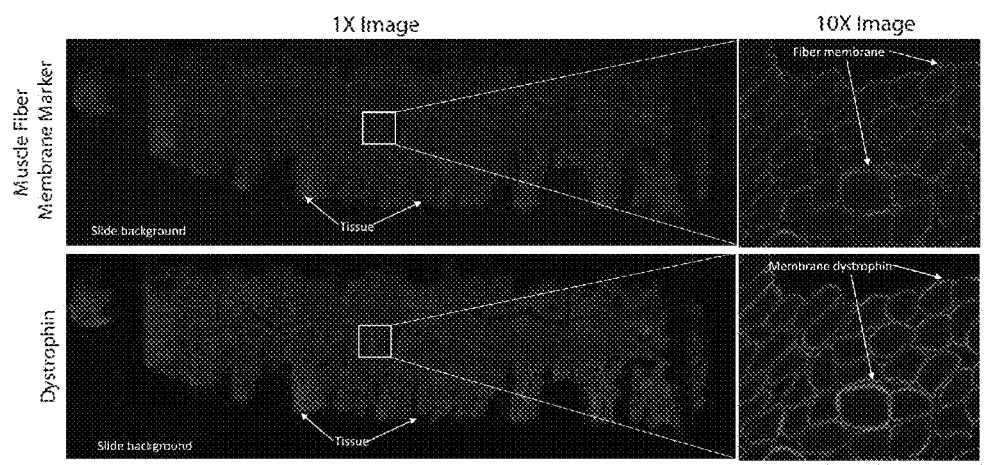
FIG. 3 provides example images of a tissue section stained for a biomarker of the muscle fiber membrane and dystrophin and visualized with fluorescence labeled probes.

FIG. 3 demonstrates the result of the preferred method of histology staining for this invention. The histologic processing and staining produced a dual color image of a muscle biopsy tissue section. Dystrophin protein levels are visualized using a red fluorescence detection probe and the biomarker of the muscle fiber membrane (e.g. merosin) is highlighted with a green detection probe. Each color channel capturing the respective biomarker is shown as separate images, but may be displayed as a single overlay of both color channels.

Slide Digitization

Histology slides can be digitized using commercially available digital microscopes and/or slide scanners (e.g. Aperio, Cri, Hamamatsu, Leica, Omnyx, Philips, Ventana and 3DHistech). Different imaging acquisition techniques (e.g. bright-field, fluorescence, multi-spectral, polarized) can be used to create a digital image of a histology slide. In some cases, different image acquisition techniques can be applied to the same histology slide, resulting in multiple images for a single slide. The digitization of a slide can have a considerable effect on how the cell features of interest are imaged. Thus, careful control needs to be applied to standardize this process.

Figure 4:
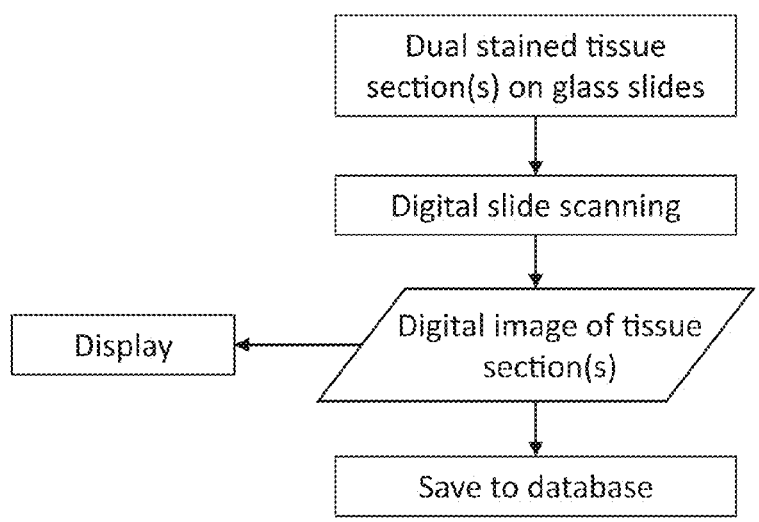
FIG. 4 provides an example of steps for generating digital images of the dual stained tissue sections, and saving said sections to a database.

FIG. 4 provides a schematic for the slide scanning process, whereby dual stained tissue sections are digitized using a digital slide scanner and saved to a database. Images can be saved directly to a database, or can be displayed and reviewed for quality. In a preferred embodiment of this invention, dual fluorescence stained tissue section slides are digitized using a fluorescence slide scanner.

Figure 5:
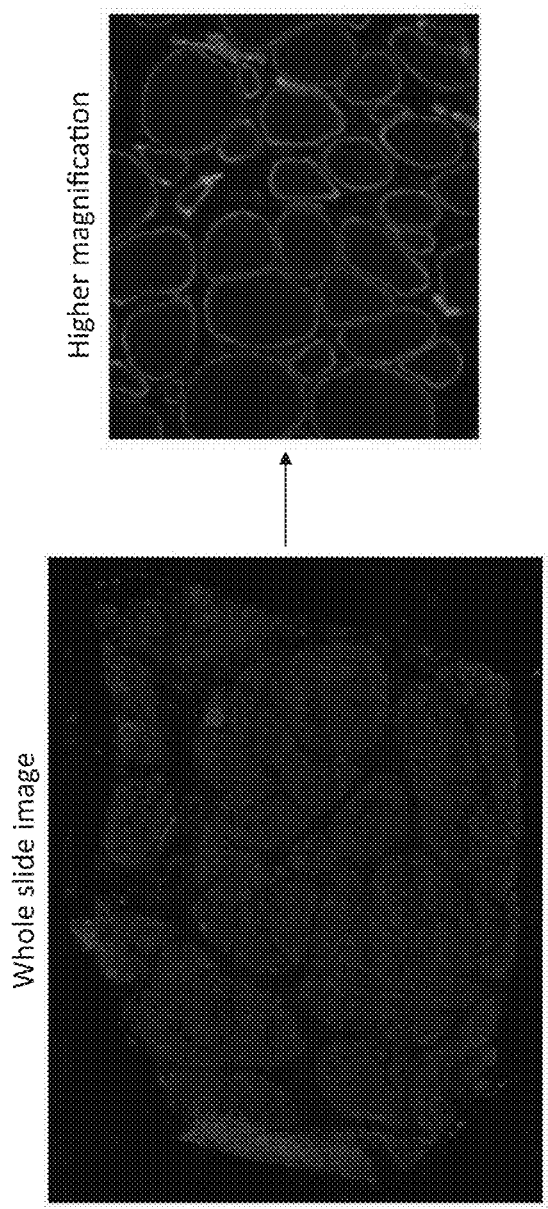
FIG. 5 shows an example digital image of a dual fluorescence stained tissue section after digital slide scanning with the red and green image channels overlaid.

FIG. 5 shows the result of scanning a tissue section stained for two biomarkers and visualized with fluorescent reagents using a fluorescence slide scanner. Shown is a whole slide digital image of the tissue section with the red and green fluorescent image channels overlaid alongside a higher magnification view of said tissue section.

Imaging System Calibration Using Fluorescence Reference Materials:

Quantification of staining intensities and distribution can be challenging for digital images generated from fluorescence stained tissue sections. One potential source for this challenge is the stability of the components of fluorescent imaging systems (i.e. light source output, camera, exposure times, etc.). The components of the imaging system (e.g. light source) can be prone to drift which ultimately impacts upon the assessment of fluorescent signal. Therefore, in an embodiment of this invention, optional scanning of a fluorescent reference material (e.g. auto-fluorescent plastic) can be performed prior to scanning fluorescently labeled tissue sections to assess instrument drift.

The fluorescence intensity (FI) values for the reference material can be compared with expected values to determine the level of instrument drift. Ultimately, the comparison of the measured and expected values can be fed forward into an algorithm process as calibration parameters prior to evaluating digital images of tissue sections submitted for evaluation.

The fluorescence reference material can be any material which fluoresces upon incident light, and has a fluorescence that is reproducible and can be characterized. Examples of potential fluorescent reference materials include, but are not limited to: quantum dots, auto-fluorescing plastics, plastics made from or doped with fluorescing materials, thin fluorescent films, and stable fluorophores.

Figure 6:
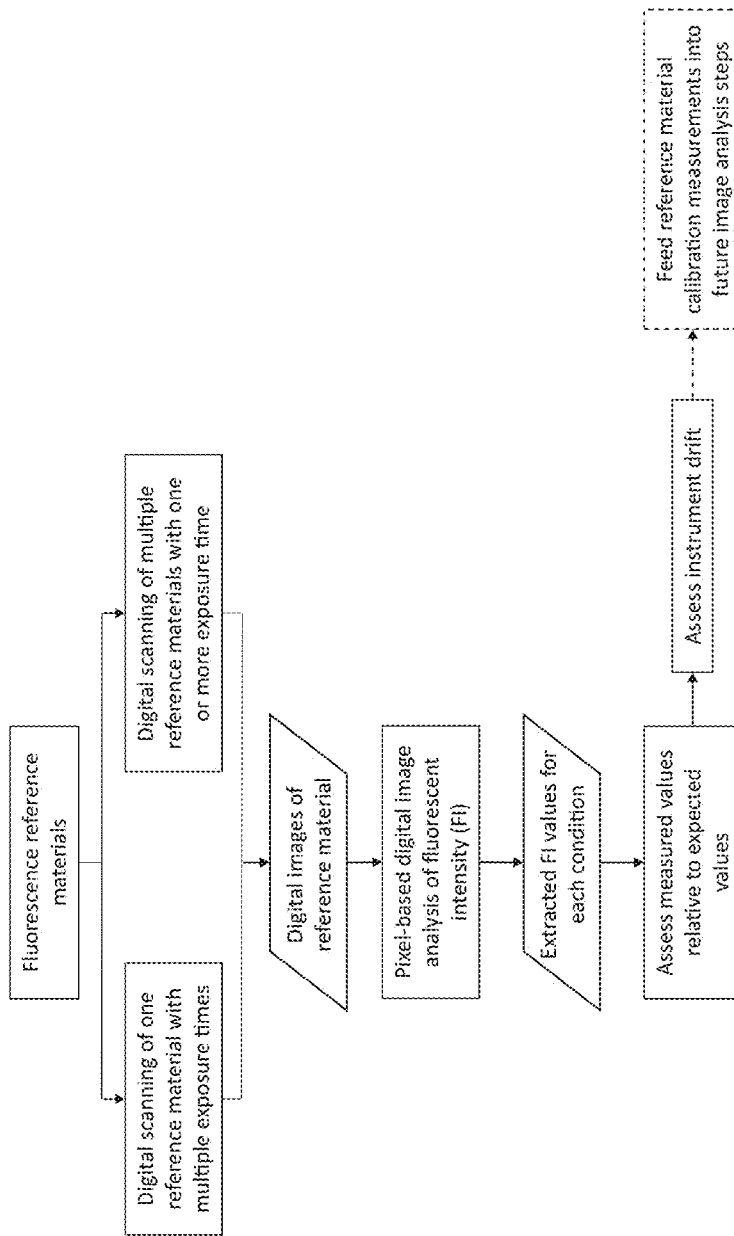
FIG. 6 demonstrates the process by which a fluorescent reference material is used to assess imaging system instrument drift for optional use in fluorescence instrument calibration.

FIG. 6 outlines the use of fluorescent reference materials to assess instrument drift with the intent of establishing calibration parameters that can be monitored and fed forward into an algorithm process. In this illustrative example, a reference material is scanned with a variety of image capture exposure times, or where multiple reference materials are scanned with one or more exposure time, and digital image analysis is used to assess FI values. The measured FI values are compared with expected values to assess instrument drift and to generate calibration parameters for use in an algorithm process.

Figure 7:
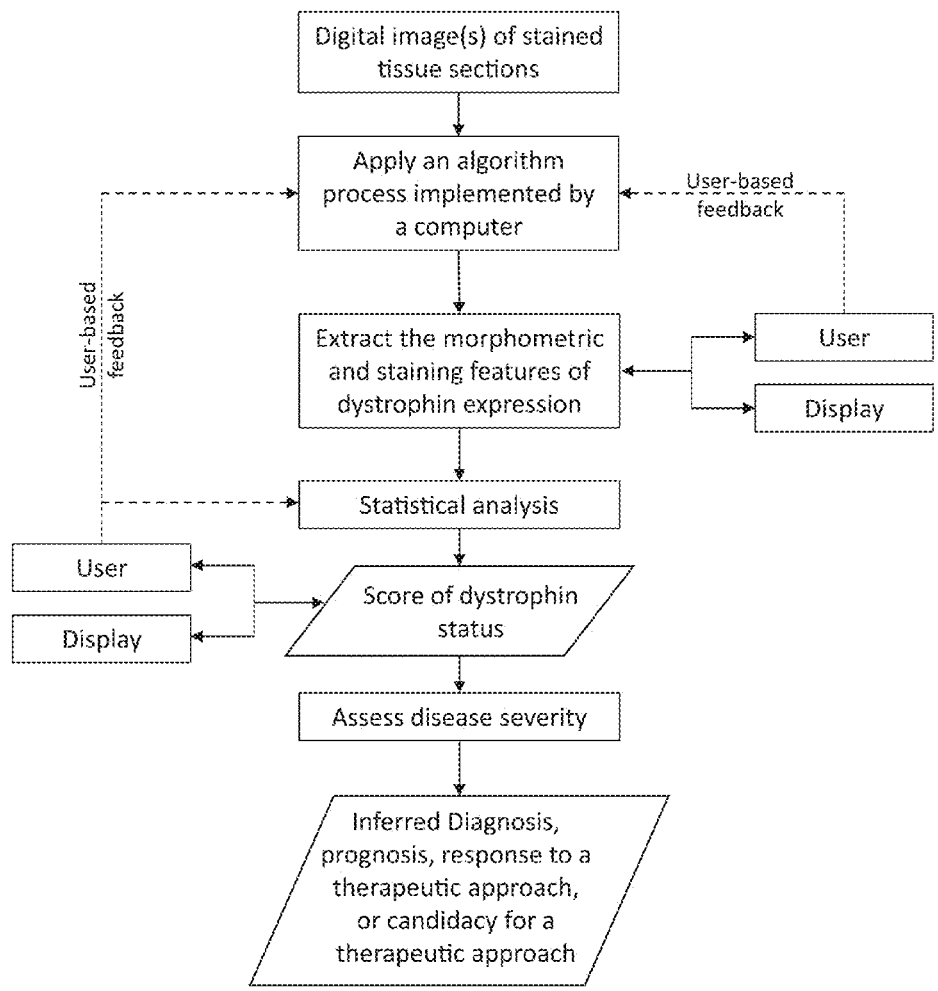
FIG. 7 illustrates the process by which an algorithm process implemented by a computer is applied to digital images of stained tissue sections to assess muscular dystrophy disease severity based on dystrophin expression.

Digital Image Analysis of Dystrophin Expression in Muscle Fibers:

FIG. 7 illustrates the general method of scoring muscular dystrophy disease status by applying an algorithm process implemented by a computer to digital images of stained muscle tissue sections. For purpose of example and not limitation, the algorithm process is applied to assess dystrophin protein expression. In this embodiment, an algorithm process implemented by a computer is applied to each image and extracts the morphometric and staining features of the tissue section and individual muscle fibers within the tissue section. The analysis results can be displayed as an overlay on the original or a post-processed image for review. Optionally, the user can integrate feedback into the algorithm process after reviewing the analysis results to refine or improve the algorithm process. The features extracted by the algorithm process are analyzed with statistical methods to derive a score of the dystrophin status for each patient. The results of this analysis are displayed for user review and the user may modify the algorithm process or statistical analysis approaches based on said review. Inferences of diagnose, prognosis, response to a therapeutic approach, or selection of patients as candidates for a specific therapy are made based on the score of dystrophin status.

In an embodiment of this invention, the algorithm process is conFIG.d to assess images of dual stained tissue sections. The tissue sections can be stained with chromogenic or fluorescence probes for muscular dystrophy-linked protein expression and a biomarker of the muscle fiber membrane. The algorithm process splits (i.e. de-convolutes two chromogenic stains from a bright-field image, separates the red from green fluorescence channels for a fluorescent image, etc.) the original image into two separate images or image layers; one image or layer containing, for example, dystrophin staining information and the second image or layer containing the staining information for the biomarker of the muscle fiber membrane.

In a preferred embodiment of this invention, the image or image layer containing the staining information for the biomarker of muscle fiber membranes is assessed using an algorithm process to detect and classify individual muscle fibers. The algorithm process then generates a muscle fiber membrane mask. This mask is displayed as an overlay on the original image of the tissue section, or on the muscle fiber membrane biomarker image or image layer, and reviewed by the user. The user may modify the algorithm process to improve detection and classification of individual muscle fiber membranes.

Figure 8:
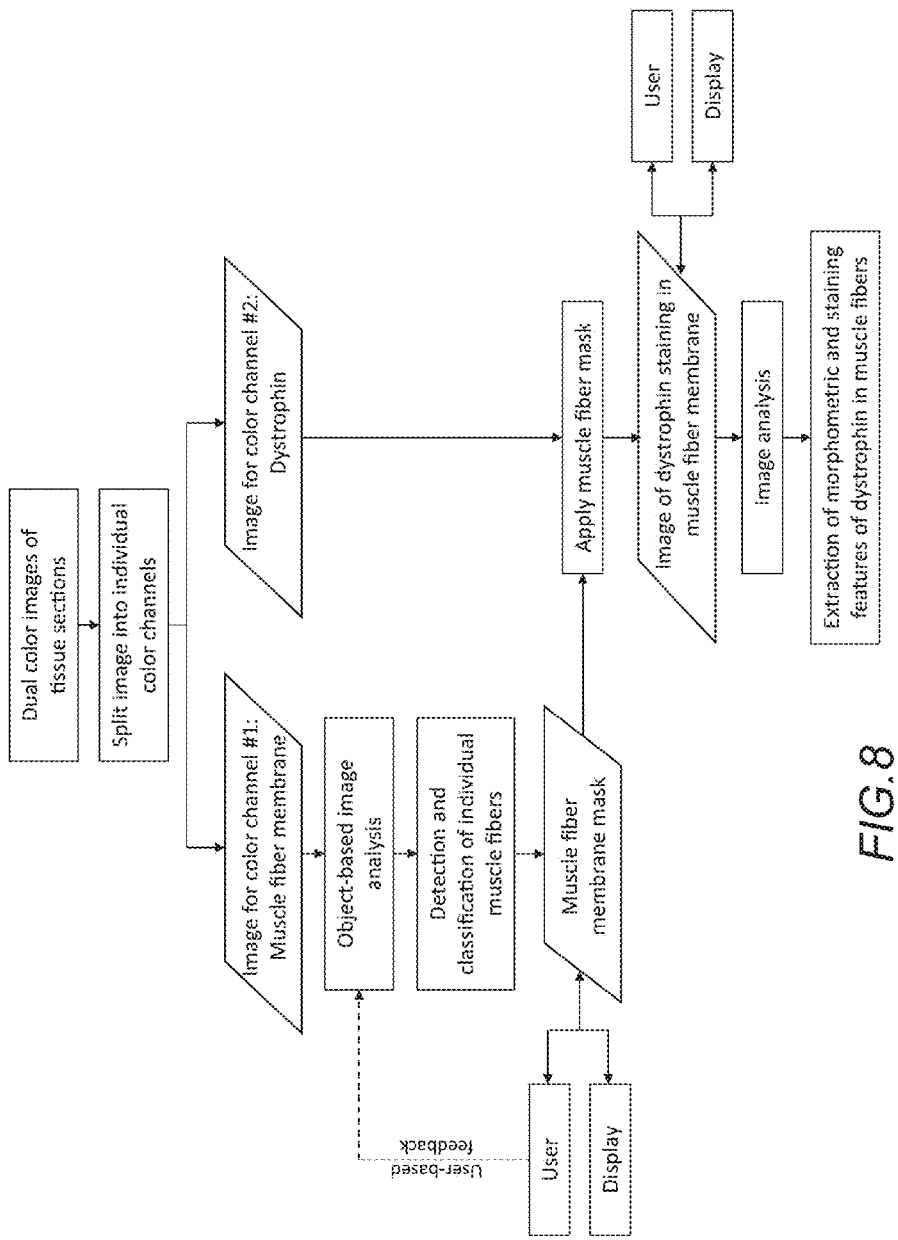
FIG. 8 illustrates the process by which a muscle fiber mask is generated using the biomarker of muscle fiber color channel, and the process by which the mask is applied to the dystrophin color channel to enable extraction of the morphometric and staining features of dystrophin in the muscle fiber membrane by the algorithm process.

The resulting muscle fiber mask is applied to, for example, the dystrophin image or image layer to produce an image of dystrophin staining only in the muscle fiber membrane. The staining and morphometric features of dystrophin expression are extracted using the algorithm process implemented by a computer system. FIG. 8 illustrates this preferred embodiment of the invention.

Figure 9:
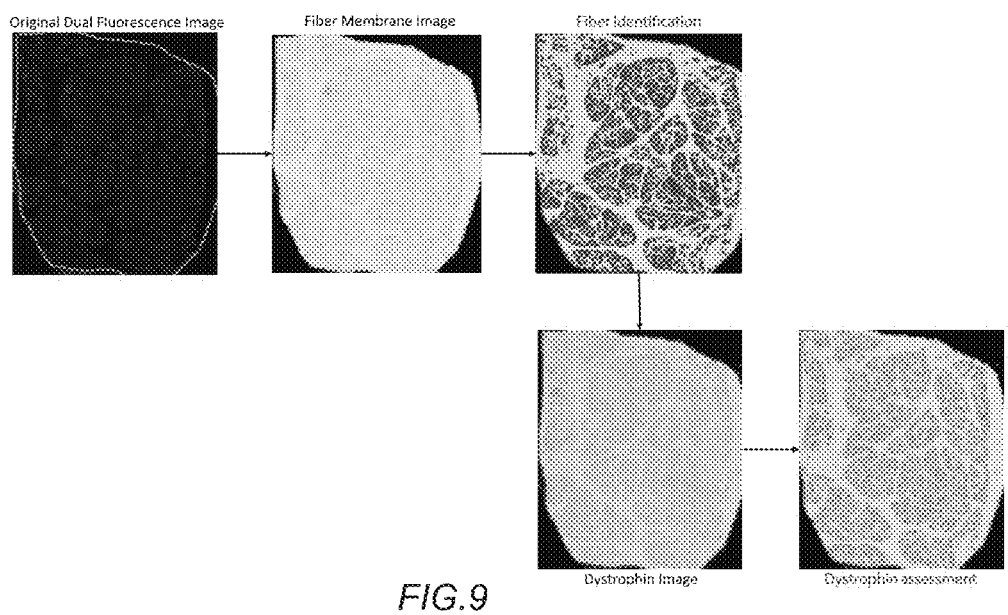
FIG. 9 provides example images demonstrating the processing of the original digital image of dual fluorescent channels to assess dystrophin staining and morphometric features using the algorithm process.

FIG. 9 shows example images of the steps implemented by the preferred embodiment of the invention, and describes the application of the algorithm process implemented by the computer to a dual fluorescence image of dystrophin and a biomarker of muscle fiber membranes. The original fluorescent image is split into the biomarker of fiber membrane layer (green), and the algorithm process identifies and classifies each muscle fiber (blue overlay). The muscle fiber mask is applied to the dystrophin image layer (red), and the morphometric and staining features of dystrophin are extracted by the algorithm process implemented by a computer and stored in a database for future analysis. The analysis and scoring of dystrophin staining in muscle fibers is displayed (multi-color overlay) on an image of the tissue section.

In another embodiment of this invention, a single stained tissue section is digitized and analyzed by the algorithm process. The image layer containing the, for example, dystrophin staining information is assessed by the algorithm process to detect and classify muscle fibers. The algorithm process then extracts the morphometric and staining features of dystrophin and stores said features in a database for future analysis.

Figure 10:
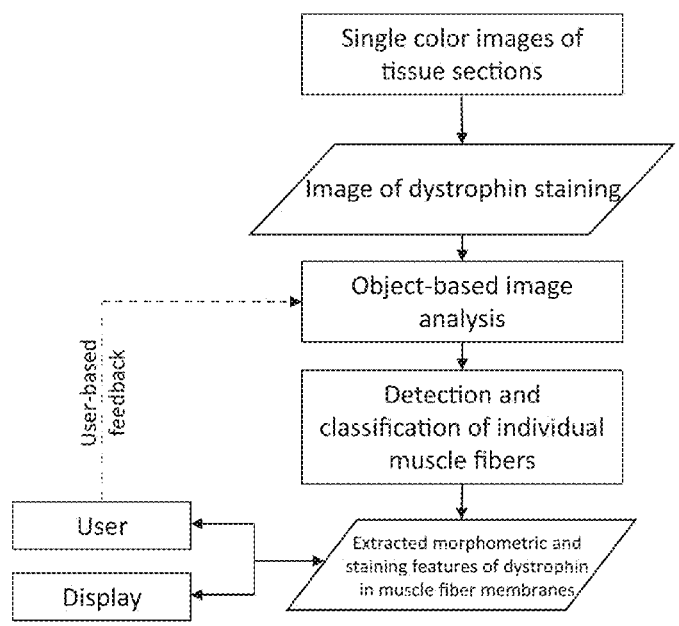
FIG. 10 illustrates the process by which an image of a single fluorescence (dystrophin) stained tissue section is processed to extract the morphometric and staining features of dystrophin staining using an algorithm process.

FIG. 10 illustrates this embodiment of the invention whereby the algorithm process is conFIG.d to extract the morphometric and staining features of muscular dystrophy-linked proteins in muscle fiber membranes. The results of the analysis can be displayed as an overlay on the original, or subsequently processed image, of the tissue section for assessment by a user. The user's review of the analysis can be used to assess the accuracy of the analysis by the algorithm process, and modifications can be integrated into the algorithm process based on user feedback.

Detection of individual muscle fibers, and the surrounding muscle fiber membrane, is a crucial component for both the single and dual stained tissue section algorithm process modes. Three phases of image processing steps are implemented by the algorithm process to accurately identify each muscle fiber for subsequent analysis of muscular dystrophy-associated protein quantification (i.e. quantification of dystrophin expression). Specifically, the image processing steps identify and outline the muscle fiber membrane for each detected muscle fiber.

Figure 11:
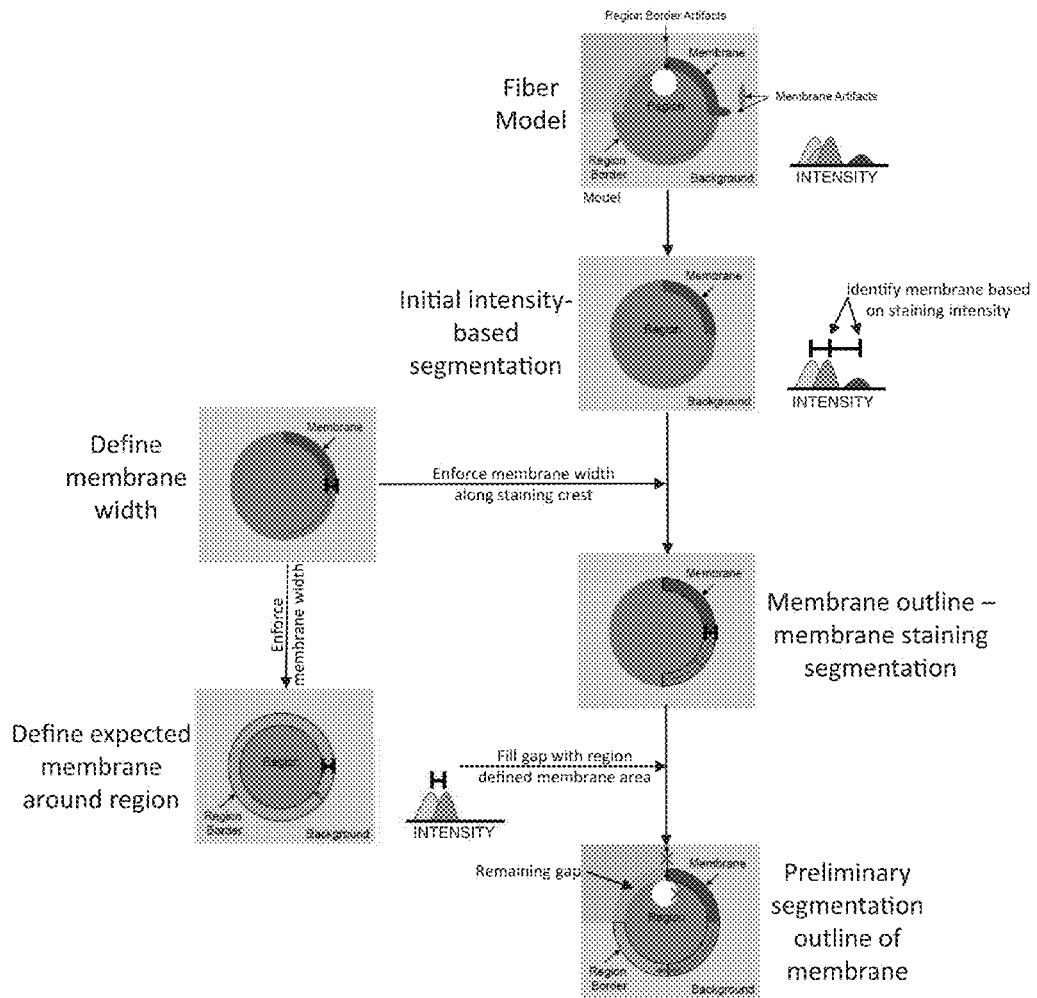
FIG. 11 demonstrates the first phase of image processing steps implemented by the algorithm process to identify the muscle fiber membrane using staining intensity-based image segmentation.

FIG. 11 demonstrates the first phase of image processing steps which lead to a preliminary segmentation of muscle fiber membranes. Staining in muscle fibers can present in a number of different ways, and these different presentations are illustrated in FIG. 11. Fiber membrane staining (i.e. merosin, dystrophin, etc. staining) can be distinguished from background staining and staining within the fiber (region). The initial segmentation of fiber membranes based on staining intensities can identify and outline the membrane area based on the abovementioned staining differences. In instances where the staining presents as a narrow crest rather than a wider membrane-like object, an average membrane width is enforced to outline the membrane area in these regions. Subtle staining intensity differences between the background and interior fiber region are typically observed, and these staining differences can be utilized to identify the boundaries of the region. By extension, the membrane is then defined around the outer boundary of the region using a defined membrane width, and is used to fill in a portion, or all, of a remaining gap in the fiber membrane area. These processes, outlined in FIG. 11, result in a preliminary segmentation and outlining of the muscle fiber membranes. Gaps in the outline of the membranes may still exist after this initial segmentation.

Figure 12:
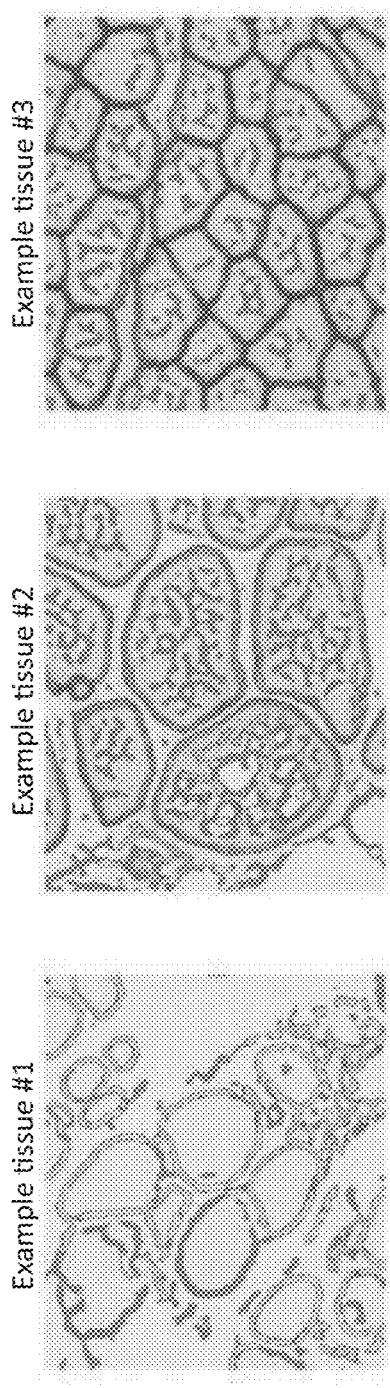
FIGS. 12(A-C) each provide one of three examples of muscle fiber membrane identification using the first phase of image processing steps implemented by the algorithm process.

FIG. 12 illustrates the results of the initial segmentation and outlining image processing phase. The area of the muscle fiber membrane identifiable by staining intensity differences are outlined in dark green lines, while membranes defined based on the region within each fiber are colored by solid, lighter green lines. FIG. 12 demonstrates that some gaps in muscle fiber membranes may not be resolved by the first phase of image processing steps and that a number of false positive membranes, or membrane segments, are identified.

Figure 13:
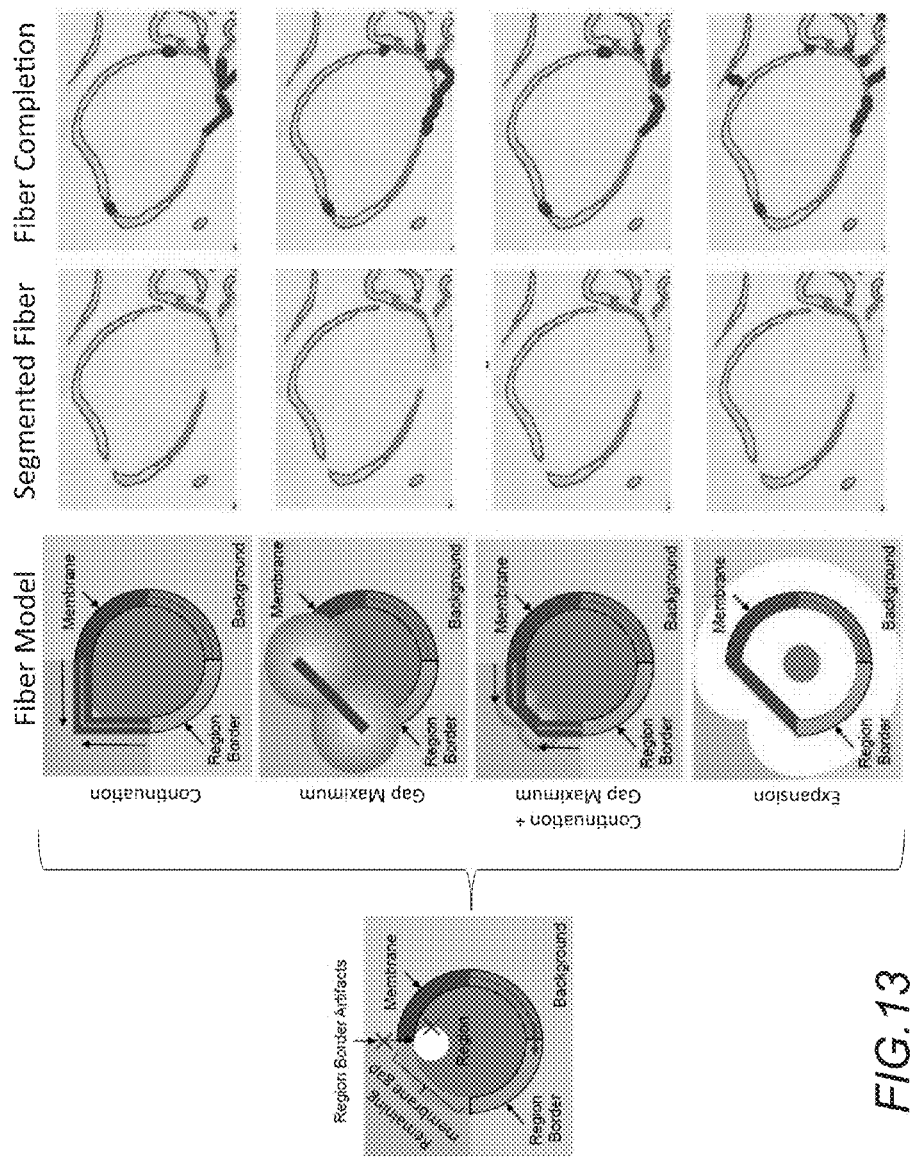
FIG. 13 illustrates the various second phase image processing steps implemented by the algorithm process to close any remaining gaps in incompletely identified muscle fiber membranes.

The second phase of image processing steps are implemented by the algorithm process to close any remaining gaps in individual muscle fiber membranes. FIG. 13 illustrates the possible steps which can be implemented by the algorithm process to complete each muscle fiber membrane where gaps exist. In an illustrative embodiment, one processing step utilizes a linear continuation of muscle fiber membranes at points where gaps occur with endpoint detection to identify the intersection of the two membrane continuations. Another processing step utilizes a gap maximum to associate two fiber membrane ends with each other. A linear connection is formed between each membrane end within the gap maximum distance. Both the continuation and gap maximum processing steps can be combined to define a connection between two membrane ends which better represents the expected shape of a muscle fiber membrane (i.e. a smooth, curved connection). Finally, an expansion region around an existing fiber membrane outline can be placed, and points of convergence between membrane objects included by the expansion region can be used to identify fiber membrane ends which belong to the same fiber. A linear or curved connection can then be defined between the two muscle fiber ends. In FIG. 13, blue lines identify the areas of the muscle fiber which are completed after applying the second phase of image processing steps to each muscle fiber in an image.

Figure 14:
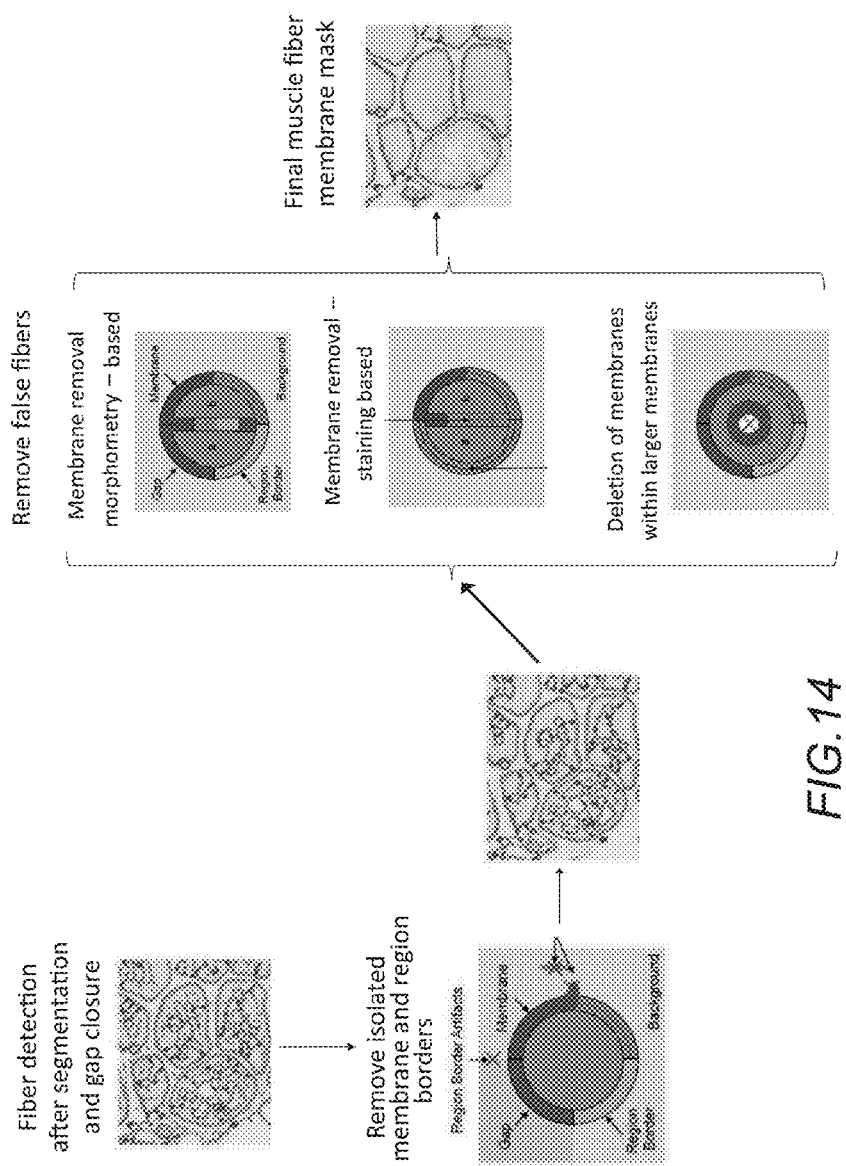
FIG. 14 illustrates the tertiary phase image processing steps implemented by the algorithm process to remove falsely identified muscle fiber membranes and fiber membrane segments leading to a final mask of the muscle fiber membranes in an image.

The first two phases of image processing steps accurately identify true muscle fiber membranes, but also identify a number of false positive membranes and membrane segments. Both the accurate detection of muscle fibers and detection of false positive membranes are illustrated in FIG. 14. FIG. 14 illustrates the third phase of image processing steps which remove false positive membranes while leaving behind and reinforcing true positive membranes. These processing steps function to first remove isolated membranes and region borders which represent unconnected false positive membrane segments. Additional processing steps are implemented to remove fibers based on one or more of: morphometric criteria (e.g. fiber roundness criteria), staining criteria (e.g. comparison of staining crest intensity relative to a mean value for the image), and fiber membranes which reside within larger fiber objects. The application of these image processing steps, in addition to the phase one and two image processing steps, result in a final muscle fiber membrane mask. The membrane mask can be defined on an area basis (e.g. total muscle fiber area), or defined on an object basis (e.g. each muscle fiber is an object).

The morphometric and staining features of a muscular dystrophy-associated protein can be assessed once the muscle fiber membrane regions have been defined. These features can be assessed across the total area of the image, within the membrane area defined by image processing steps, or on a muscle fiber-by-fiber basis.

The morphometric features of the muscular dystrophy-linked staining pertain to the physical presentation of, for example, dystrophin distribution across the tissue section and within muscle fibers (i.e. texture of dystrophin distribution across the whole slide, completeness of dystrophin staining within the membrane area of a muscle fiber, texture of dystrophin distribution within the membrane area of a muscle fiber, etc.), and the physical presentation of the muscle fibers (i.e. size, shape, uniformity in shape, etc.) as visualized by dystrophin or the biomarker of muscle fiber membrane staining. Staining features pertain to the presentation of stains on a slide (i.e. dystrophin staining intensity, texture of dystrophin staining intensity across the tissue section or within a muscle fiber membrane, etc.).

Ultimately, the morphometric and staining features are interrelated due to the assessment of morphologic features based on the presentation of staining. The individual morphometric and staining features can be grouped into three general categories which characterize muscular dystrophy-linked protein expression relative to specific tissue features.

Figure 15:
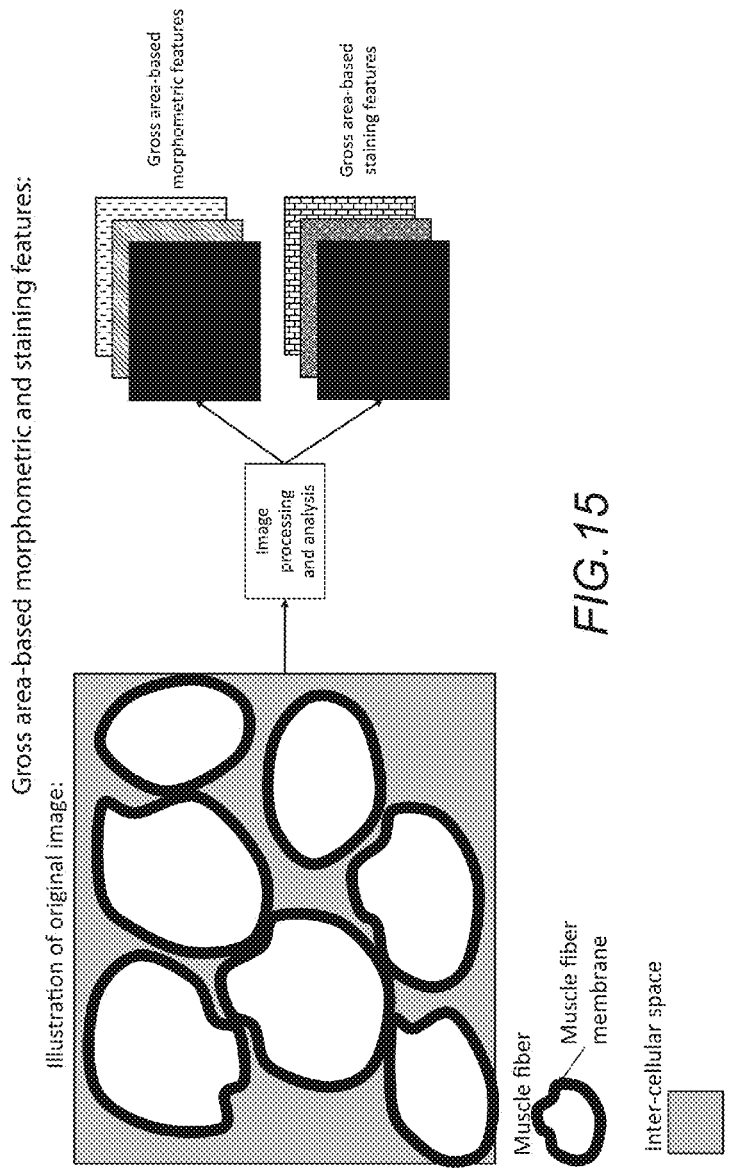
FIG. 15 illustrates the gross assessment of dystrophin staining across the total area of a digital image of a tissue section.

The first category of features pertain to the general presentation of muscular dystrophy-linked staining (i.e. average staining intensity for the image, maximum staining intensity for the image, median staining intensity for the image, etc.) and distribution (i.e. Fourier frequency spectrum of staining distribution, texture of staining distribution across the tissue section, uniformity of staining distribution across the tissue section, etc.) over the area of the tissue section being evaluated. FIG. 15 illustrates the concept of this category of features. Features are assessed without defining and identifying muscle fiber objects.

The second category of features relate to muscular dystrophy-linked staining features (i.e. mean staining intensity, the percentage of membrane area at negative, low, medium, and high staining levels, staining texture heterogeneity within the membrane area, etc.) only within the area of the muscle fiber membranes. These features are not attributed to specific muscle fiber membranes, but rather are assessed relative to the total area of the muscle fiber membranes. For this category of features, a mask of the muscle fiber membranes is created to identify the muscle fiber membrane area.

Figure 16:
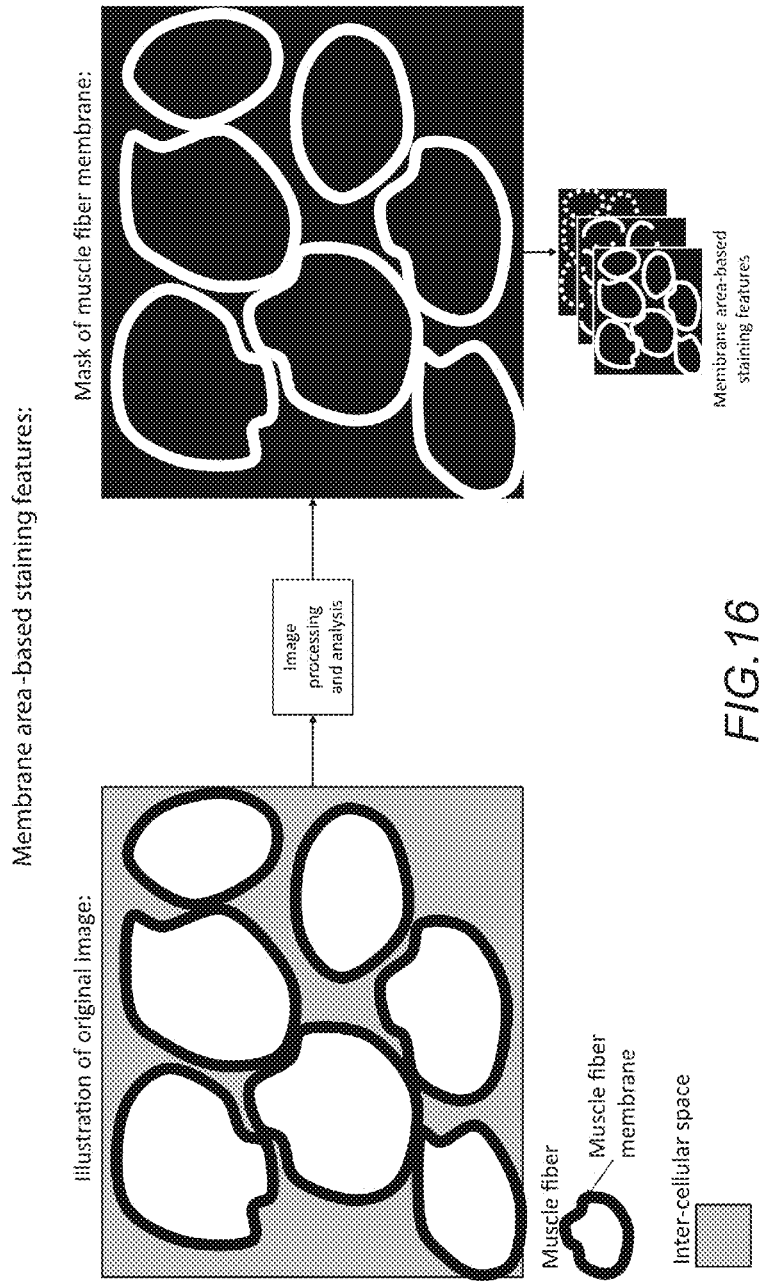
FIG. 16 illustrates the assessment of dystrophin staining across the total muscle fiber membrane area defined by the muscle fiber membrane mask.

For example, dystrophin staining is assessed only within the muscle fiber membrane area of the mask. FIG. 16 illustrates this category of features.

Figure 17:
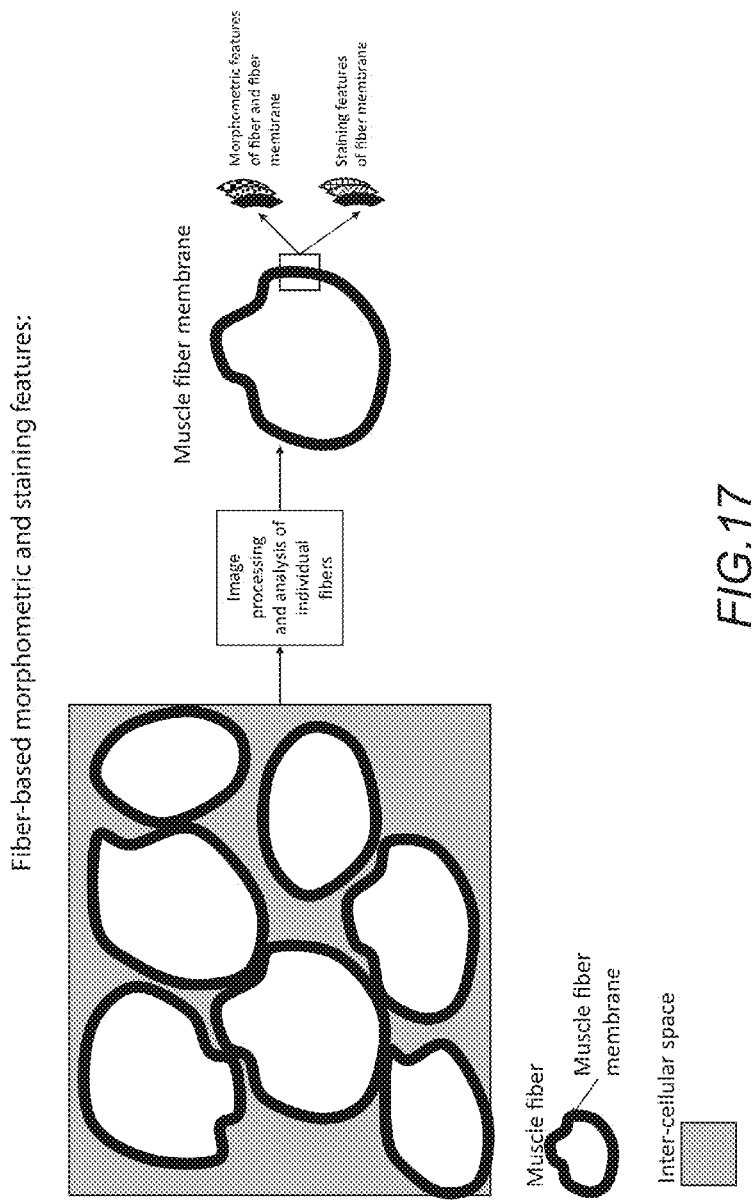
FIG. 17 illustrates the assessment of dystrophin staining in an object-by-object manner for each muscle fiber identified in the area of the digital image of a tissue section.

The third category of features relate to the muscular dystrophy-linked protein staining and morphometric features assessed on a muscle fiber-by-fiber basis. For this category of features, each muscle fiber identified by the algorithm process is characterized by staining (i.e. mean dystrophin staining intensity, maximum dystrophin staining intensity, etc.) and morphometric (i.e. completeness of dystrophin staining, average width of fiber membrane, length of fiber membrane, uniformity in width of the fiber membrane, etc.) features of the muscular dystrophy-linked proteins within said fiber's membrane. Each fiber-by-fiber feature can be summarized for the tissue section (i.e. average membrane staining intensity, average completeness of dystrophin staining, etc.), or a sub-region of the tissue section, to capture the histogram statistics of said features (i.e. mean, median, mode, standard deviation, etc.). One or more features can be used (i.e. staining intensity, staining intensity plus staining completeness, etc.) to classify individual fibers on a continuous (e.g. mean value) or discrete (e.g. negative, low, medium, and high) scale. FIG. 17 illustrates this category of muscular dystrophy-linked protein staining and morphometric staining features.

Figure 18:
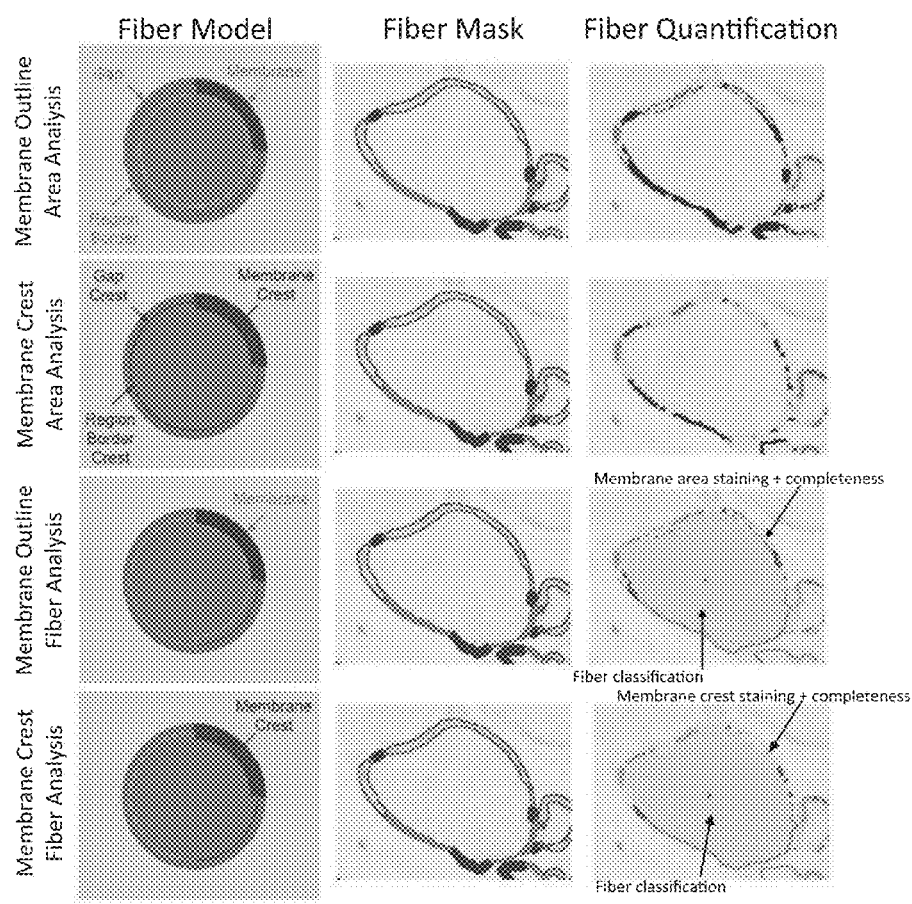
FIG. 18 provides examples of the various assessments of muscle fibers using the algorithm process to quantify staining. Staining can be assessed for the muscle fiber area based on the muscle fiber membrane mask area or along the membrane crests. Fibers can also be assessed on a fiber-by-fiber basis using morphometric and staining parameters to classify individual fibers.

FIG. 18 provides examples of the analysis approaches which assess muscular dystrophy-associated protein expression in the muscle fiber membrane area and assessment of protein expression on a muscle fiber-by-fiber object basis. Protein staining intensity is assessed within the outlined area of muscle fiber membranes, or along the muscle fiber crest area, and staining intensities are scored relative to the total muscle fiber membrane area. Staining intensity can be quantified on a continuous (e.g. intensity range 0-1) or discrete (e.g. 0, 1+, 2+, 3+ staining intensity bins) scale. Similarly, staining intensity can be assessed within the muscle fiber membrane area, or along the membrane crest area, for each muscle fiber object and each fiber can be classified on a continuous (e.g. mean staining intensity of the fiber) or discrete scale (e.g. low staining classification). Additionally, morphometric features (i.e. completeness of staining around the membrane) can be combined with quantification of staining intensity to classify each muscle fiber within an image. In FIG. 18, staining intensity values are overlaid on the original image and color-coded relative to staining intensity and muscle fiber classification is denoted by a fill color overlaid on the interior area of the muscle fiber and color-coded relative to score. In this example, fibers are classified a score on a discrete scale (e.g. negative, low, medium, and high) which combines staining intensity and staining completeness.

Derivation of a Score of Disease Status for Each Patient:

A mathematical expression is used to combine the values for one or more parameters relating to one or more category of muscular dystrophy-linked protein expression features to derive a score of the disease status for each patient. The mathematical expression can combine values for parameters in one or more of: a linear, non-linear, and logical operator fashion. A value for an image analysis derived parameter can be one of the histogram statistics (i.e. mean, standard deviation, skewness, etc.) describing the distribution of said parameter values in the tissue.

Figure 19:
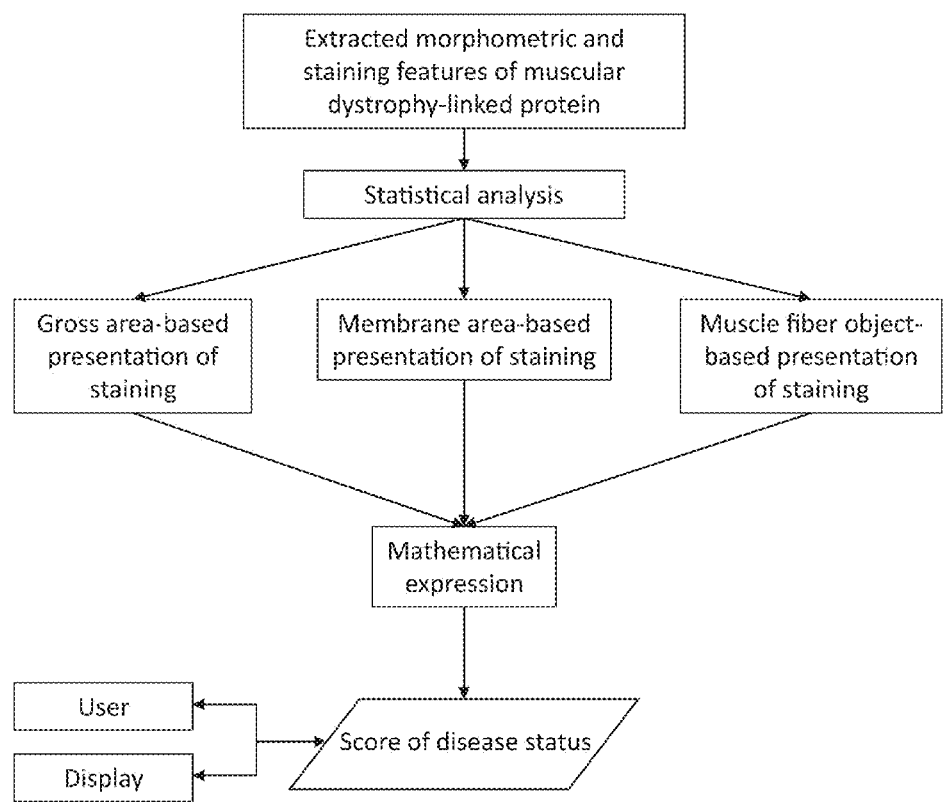
FIG. 19 demonstrates the process by which the extracted morphometric and staining features are analyzed to produce a score of muscular dystrophy disease status for each patient.

The score of disease status can be displayed through a graphical user interface and reviewed by the user of the system. FIG. 19 illustrates this embodiment of the invention whereby one or more muscular dystrophy-linked protein expression value is combined using a mathematical expression to derive a score of disease status for each patient.

Processing of Fluorescence Images for Viewing and Display of Analyses:

In a preferred embodiment of this invention, tissue sections are stained and visualized using fluorescently labeled antibodies to detect a muscular dystrophy-linked protein and a biomarker of the muscle fiber membrane. Manual scoring and review of fluorescent images is difficult due to the way in which the human eye perceives fluorescence. Specifically, assessment of fluorescent intensity is difficult to perform reproducibly with the human eye. Additionally, assessment of digital image analysis of muscular dystrophy-linked protein expression can be difficult to interpret and assess when overlaid on a dark-field fluorescence image.

Assessment of bright-field images, and chromogenic staining, are more conducive to manual assessment of staining in tissue. Additionally, overlays of analyses on bright-field images are easier to assess and interpret. Therefore, in an embodiment of this invention, fluorescent images are converted to bright-field equivalent images which mimic chromogenic staining to improve viewing and assessment of staining intensity in tissue and digital image analysis-based analyses of tissue.

Figure 20:
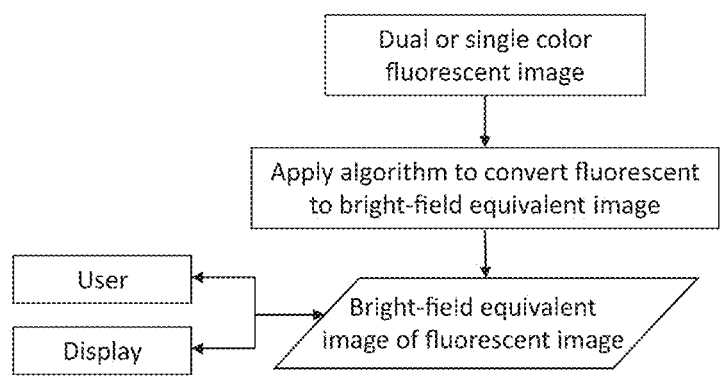
FIG. 20 demonstrates the process by which fluorescent images are converted to bright-field equivalent images for viewing and manual assessment of dystrophin staining.

FIG. 20 outlines the process by which an algorithm process is applied to a fluorescent image to covert said image to a bright-field equivalent image. The resulting bright-field equivalent image is displayed for a user to review. The algorithm process can apply one or more post-processing steps to accurately convert the fluorescent image to a bright-field equivalent image with staining intensity values depicted in a manner analogous to chromogenic stain optical density.

Figure 21:
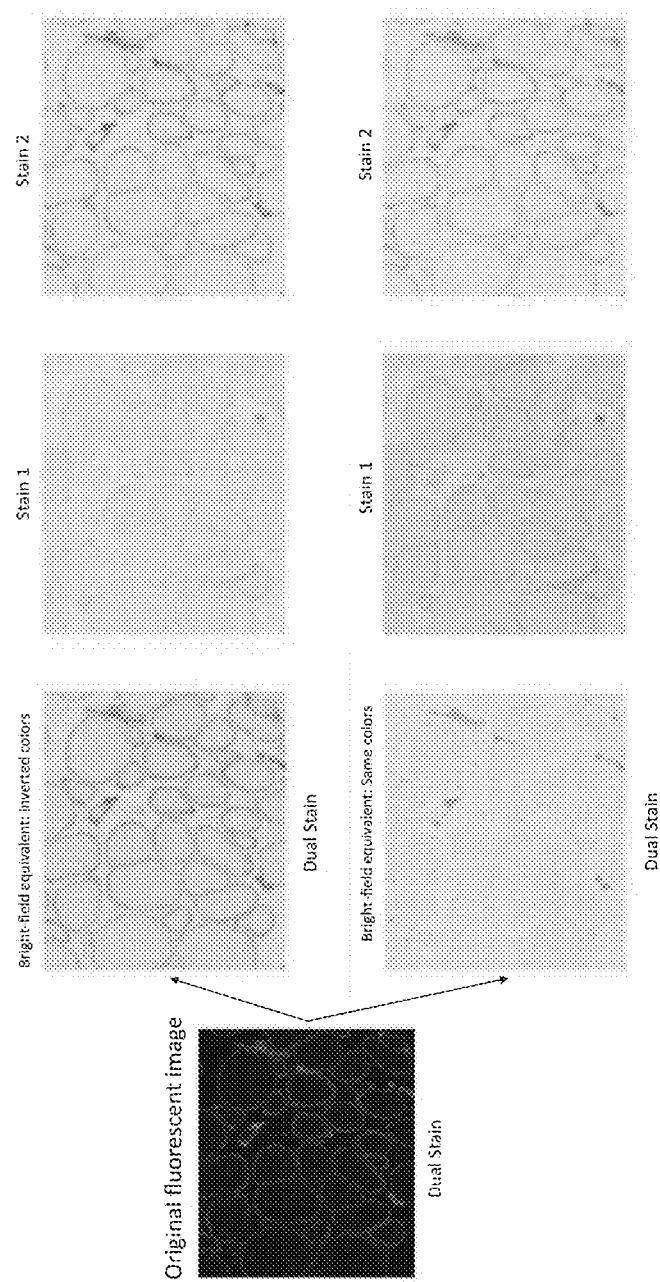
FIG. 21 provides an example of converting fluorescent images to bright-field equivalent images with, and without, color inversion.

FIG. 21 demonstrates the result of applying the algorithm process to a fluorescent image to generate a bright-field equivalent image. In an embodiment of this invention, the colors are inverted when the original fluorescent image is converted to a bright-field equivalent image. In another embodiment of the invention, the colors are kept the same when the fluorescent image is converted to a bright-field equivalent image.

Figure 22:
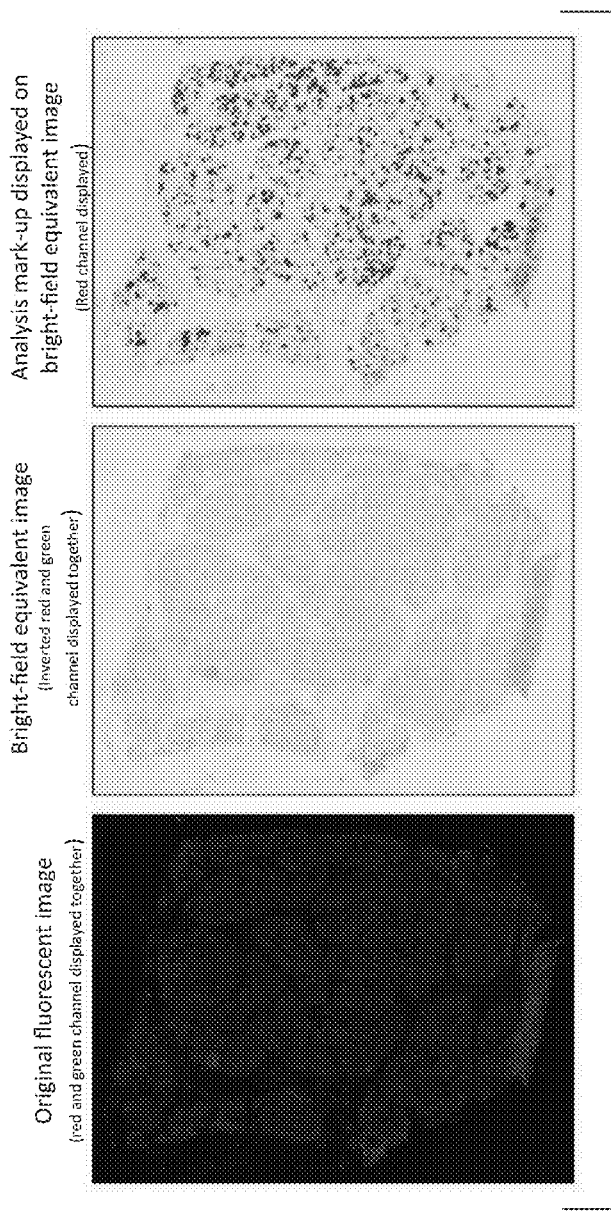
FIG. 22 shows an example of a whole slide fluorescent image displayed as a bright-field equivalent image with an analysis mark-up overlaid.

FIG. 22 demonstrates and example of applying the algorithm process to covert an original fluorescent image to a bright-field equivalent image. The analysis of dystrophin staining on a muscle fiber-by-fiber basis using an algorithm process is displayed (multi-color overlay) as an overlay on the red image layer of the bright-field equivalent image.

Figure 23:
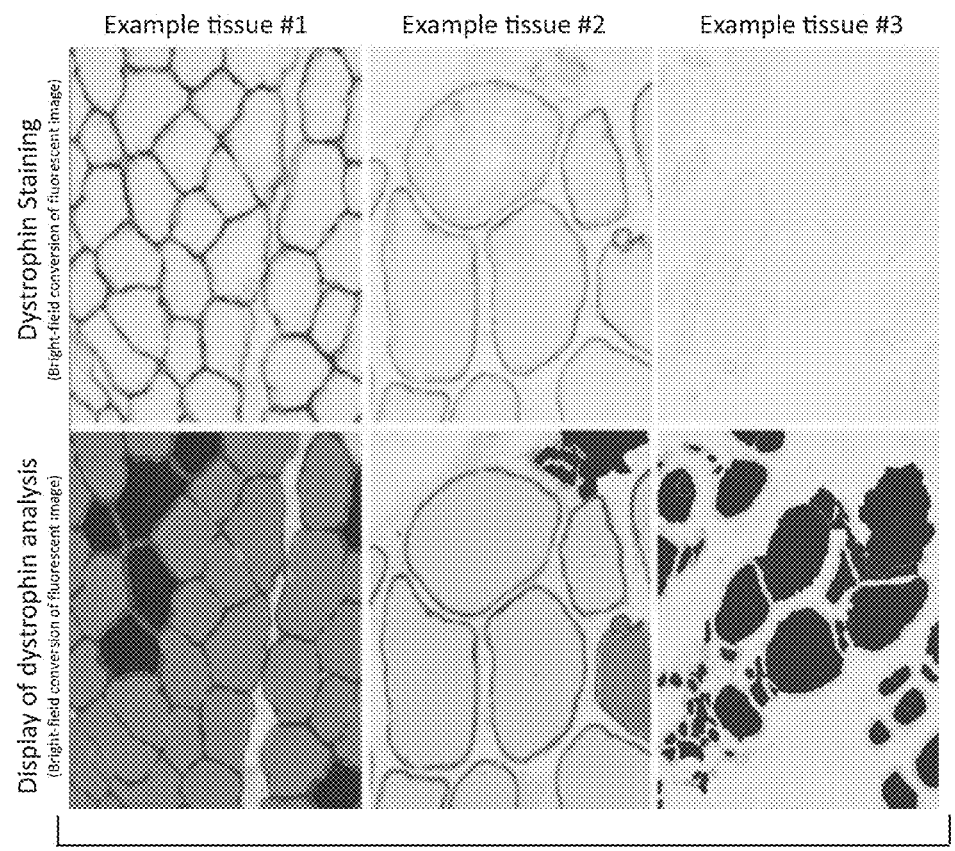
FIG. 23 provides example bright-field equivalent images of dystrophin fluorescent images with analysis mark-ups displaying the status of dystrophin expression in muscle fibers.

FIG. 23 demonstrates a higher magnification example of the bright-field equivalent image of a fluorescent image of dystrophin staining (red). The results from applying an algorithm process to a fluorescent image of dystrophin staining are displayed for the three example samples in this figure. The algorithm process characterizes dystrophin staining in the muscle fiber membrane as negative staining (blue overlay), weakly positive (yellow overlay), medium positive (orange overlay), and strongly positive (red overlay).

Figure 24:
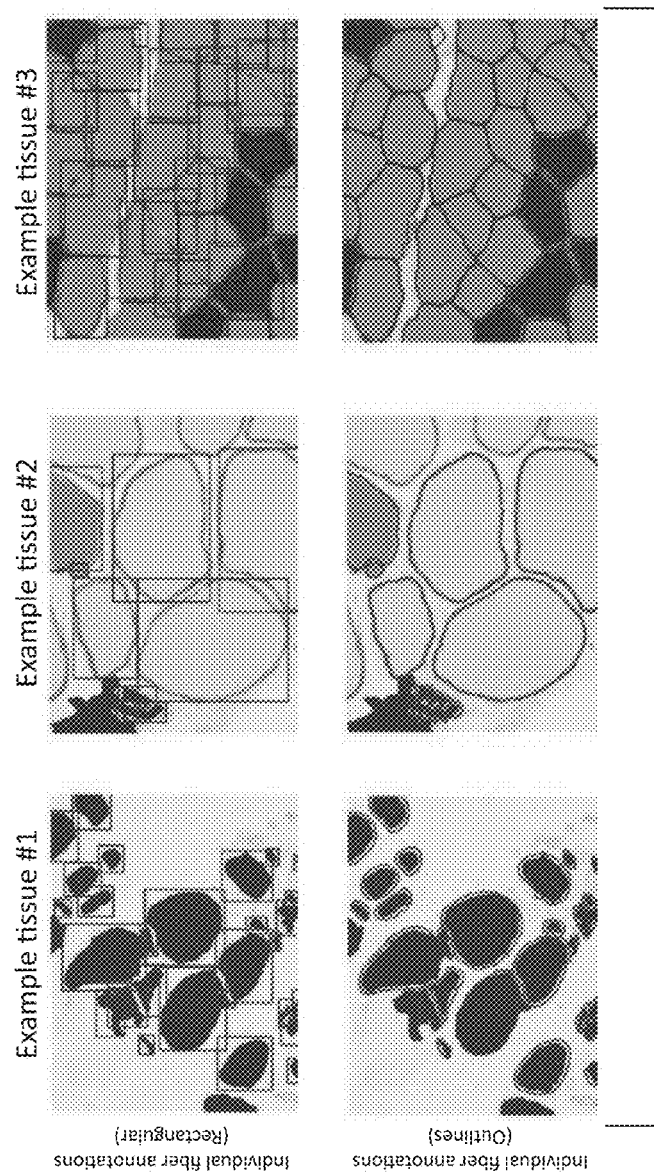
FIG. 24 illustrates the algorithm process defining regions around each muscle fiber, or the muscle fiber outline, and capturing said regions by placing individual annotations on the image of the muscle fibers.

In an embodiment of this invention, an annotation is defined for each muscle fiber object identified by the algorithm process. These annotations can outline each muscle fiber or have a rectangular geometric which encompasses the muscle fiber. FIG. 24 illustrates this embodiment of the invention and annotations are denoted by blue rectangles or outlines placed around each identified muscle fiber object.

Figure 25:
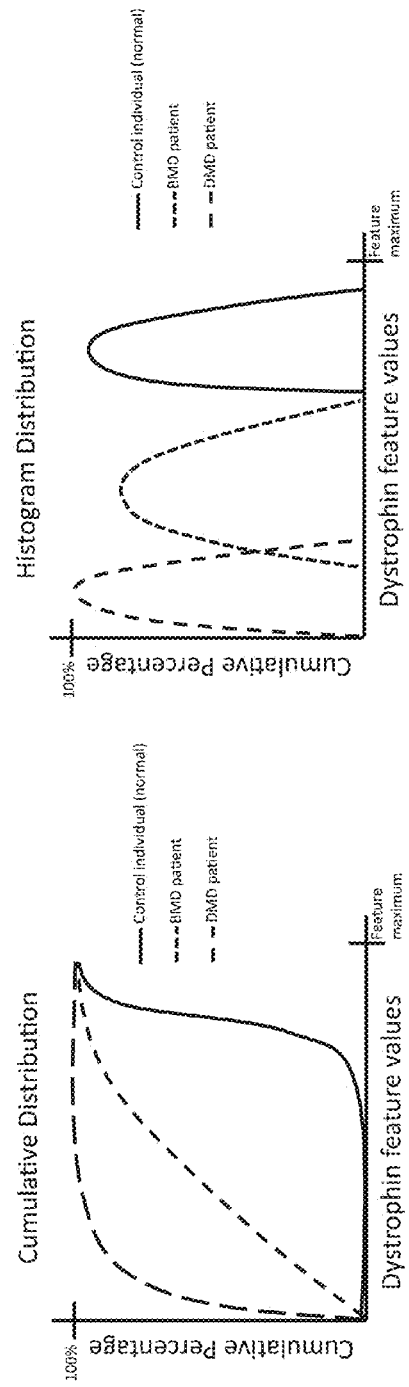
FIGS. 25(A-B) each provide illustrative examples of one of two graphical displays for assessment and scoring of the dystrophin status in muscle fibers.

Quantifying Muscular Dystrophy-Linked Protein Staining Status and Displaying Said Analysis:

The results from assessing muscular dystrophy-linked protein expression in a tissue sample can be displayed in a number of ways. For purpose of example and not limitation, FIG. 25 demonstrates two possible ways in which an image analysis-derived dystrophin expression feature for a tissue sample may be displayed. In one embodiment, the cumulative distribution of a feature value is plotted graphically and displayed to the user. In this example, features are measured on a fiber-by-fiber basis and the cumulative distribution of fiber values are displayed. The distributions can be qualitatively assessed (e.g. low, medium, high values) to derive a score the dystrophin status of a patient or mathematically assessed (i.e. Kolmogorov-Smirnov test to compare multiple CDFs, feature value at 50%, range of feature values to pass between a range of cumulative distribution values, etc.) to derive a quantitative score of the dystrophin status for each patient. In another embodiment, the histogram distribution of a feature may be displayed. The histogram distributions can be qualitatively assessed (e.g. one or more histogram statistic value) to score dystrophin staining status for a patient. Two or more statistics describing the histogram of a feature can be combined in one or more of: a linear, non-linear, and logical operator manner to derive a single score of dystrophin status for a patient.

Figure 26:
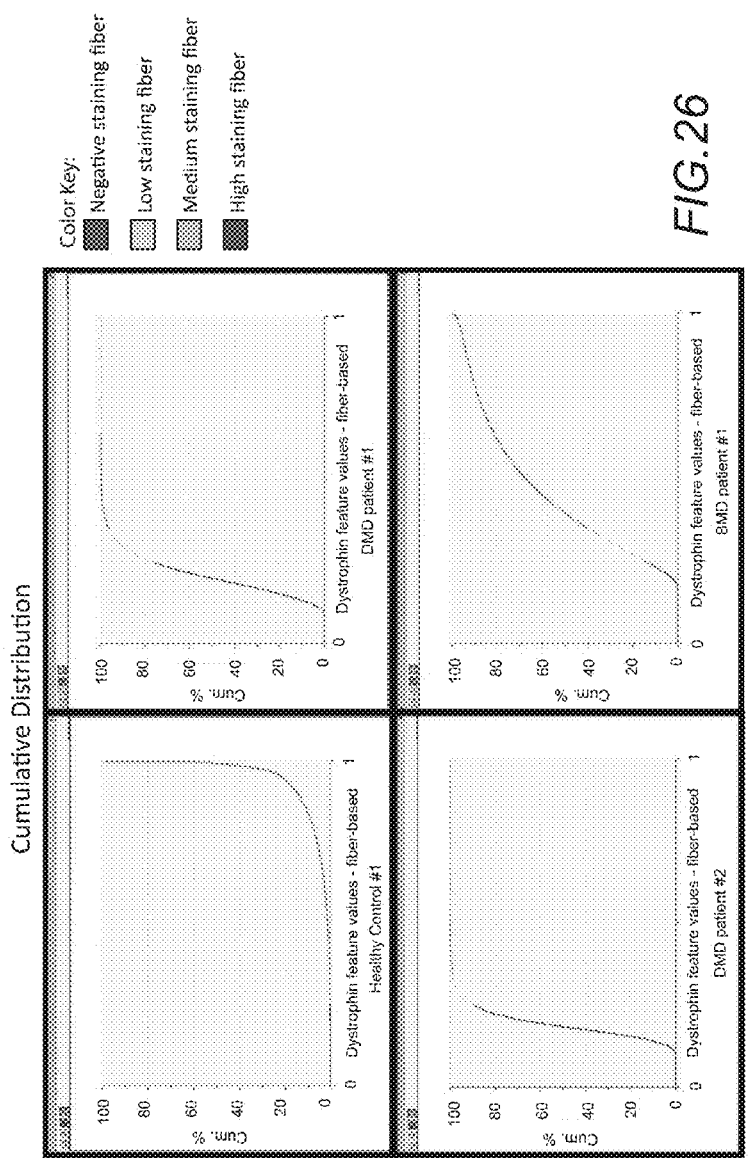
FIG. 26 provides and illustrative example of the cumulative distribution of a muscle fiber object-based dystrophin staining feature for four individuals submitted for evaluation.

FIG. 26 illustrates the output from the algorithm process applied to assess dystrophin staining levels on a fiber-by-fiber basis for four individuals. In this preferred embodiment, the cumulative distribution of a staining feature is displayed and color coded to show the relative distribution of fibers staining at negative, low, medium, and high staining levels.

What is claimed is:

1. A method for scoring muscular dystrophy-linked protein status in muscle tissue using digital image analysis, comprising:
   a. obtaining one or more muscle biopsy tissue samples from patients submitted for evaluation;
   b. processing said one or more samples to produce one or more stained tissue sections mounted on one or more glass slides;
   c. digitizing said one or more slides using a digital slide scanner or a microscope coupled with a camera to generate digital images corresponding to each of the tissue sections;
   d. displaying said digital images of said one or more stained tissue sections for visualization and review by a user;
   e. applying an algorithm process implemented by a computer to said digital images of the one or more stained tissue sections to extract staining and morphometric features of each muscle fiber within the images;
   f. for each images of the stained tissue sections, displaying results of said algorithm process overlaid on the corresponding image;
   g. combining one or more staining and morphometric feature parameters to derive a score of disease status;
   h. displaying said score in a graphical manner using a graphical user interface for user visualization and assessment; and
   i. interpreting the score of disease status to draw inferences associated with the severity of disease in each sample submitted for evaluation.

2. The method of claim 1, wherein each tissue section is stained for a muscular dystrophy-linked protein, or muscular dystrophy-linked protein and a biomarker of muscle fiber membranes.

3. The method of claim 2, wherein the muscular dystrophy-linked protein is a protein product of a gene that when mutated or otherwise disrupted gives rise to one or more muscular dystrophy disorders.

4. The method of claim 2, wherein the biomarker of muscle fiber membranes is one of: spectrin or merosin.

5. The method of claim 2, wherein the muscular dystrophy-linked protein is dystrophin.

6. The method of claim 1, wherein visualization of staining highlighting protein expression and distribution is one or more of: chromogenic and fluorescence.

7. The method of claim 1, wherein muscle fiber membranes are identified using one or more of: the muscular dystrophy-associated protein and biomarker of muscle fiber membranes staining channels.

8. The method of claim 7, wherein the muscle fibers are identified using three phases of image processing steps, including: initial segmentation, closure of gaps for incomplete membranes, and removal of false positive membranes.

9. The method of claim 8, wherein the first phase of image processing identifies fiber membranes using staining intensity differences between one or more of: fiber membrane staining, background staining outside of fibers, and staining within the interior region of a fiber.

10. The method of claim 8, wherein the second image processing phase closes remaining gaps in incomplete fibers using one or more of: fiber end continuation, gap maximum, and expansion processes.

11. The method of claim 8, wherein the third image processing phase removes false positive membranes and membrane segments by one or more of: removal of isolated fiber membrane segments and fiber region borders, removal of fiber membranes outside of morphometric feature thresholds, removal of fiber membranes outside of staining feature thresholds, and removal of fiber membranes inside a larger fiber membrane object.

12. The method of claim 1, wherein the morphometric and staining features extracted by the algorithm process pertain to characterizing the presentation of muscular dystrophy-linked protein staining in one or more of: the total area of the tissue section, the total area of muscle fiber membranes, and individual muscle fiber membranes in the tissue section in an object-based manner.

13. The method of claim 12, wherein the characterization of morphometric and staining features pertain to assessment of the full membrane width or the membrane crest.

14. The method of claim 13, wherein the membrane crest is a continuous ridge of high staining intensity values around the diameter of a muscle fiber membrane.

15. The method of claim 12, wherein staining features extracted by the algorithm process pertain to the appearance of muscular dystrophy-linked protein staining and morphometric features pertain to the physical presentation and distribution of muscular dystrophy-linked protein staining.

16. The method of claim 1, wherein one or more values relating to the morphometric and staining features of muscular dystrophy-linked protein staining are combined using one or more of: linear, non-linear, and logical operators to derive a summary score of disease status.

17. The method of claim 1, wherein the assessment of disease severity is used to determine one or more of: diagnosis of muscular dystrophy, prognosis of the normal course of disease, monitor treatment efficacy for muscular dystrophy, and selection of muscular dystrophy patients as candidates for a specific therapeutic intervention.

18. The method of claim 1, wherein digital images of tissue sections can be visualized as one or more of: bright-field images, fluorescent images, and bright-field equivalent of fluorescent images.

19. The method of claim 1, wherein the results from applying the algorithm process to assess a muscular dystrophy-associated protein in tissue are displayed as an overlay on one or more of: a bright-field image, a fluorescent image, and a bright-field equivalent of a fluorescent image of the tissue section being evaluated using a graphical user interface.

20. The method of claim 19, wherein the results are one or more of: a heat map of muscular dystrophy-linked protein staining, color classifications of muscular dystrophy-linked protein staining in individual fibers, graphical plots of muscular dystrophy-linked protein expression feature values summarized for a tissue section.

21. The method of claim 1, wherein annotations are placed around each identified muscle fiber object identified by the algorithm process.

22. The method of claim 21, wherein the annotations can be a rectangular geometry or an outline fit to the shape of each fiber.

23. The method of claim 1, wherein calibration values are integrated into the algorithm process prior to assessment of the patient samples based on one or more of: a reference material digitally scanned with the imaging system used in a study and a reference tissue stained with an identical staining protocol used in the study and digitally scanned.

* * * * *